(12) United States Patent
Black et al.

(10) Patent No.: US 8,796,297 B2
(45) Date of Patent: Aug. 5, 2014

(54) 4-SUBSTITUTED-2-AMINO-PYRIMIDINE DERIVATIVES

(75) Inventors: Lawrence A. Black, Libertyville, IL (US); Gregory A. Gfesser, Lindenhurst, IL (US); Marlon D. Cowart, Round Lake Beach, IL (US)

(73) Assignee: AbbVie Inc., North Chicago, IL (US)

( * ) Notice: Subject to any disclaimer, the term of this patent is extended or adjusted under 35 U.S.C. 154(b) by 49 days.

(21) Appl. No.: 12/828,104

(22) Filed: Jun. 30, 2010

(65) Prior Publication Data

US 2010/0331294 A1   Dec. 30, 2010

Related U.S. Application Data

(60) Provisional application No. 61/221,555, filed on Jun. 30, 2009.

(51) Int. Cl.
*A01N 43/54* (2006.01)
*A61K 31/505* (2006.01)

(52) U.S. Cl.
USPC .......................................... 514/275; 544/331

(58) Field of Classification Search
USPC .......................................... 544/331; 514/275
See application file for complete search history.

(56) References Cited

U.S. PATENT DOCUMENTS

| | | | |
|---|---|---|---|
| 2,455,396 A * | 12/1948 | Adams et al. ................. | 544/323 |
| 8,268,846 B2 * | 9/2012 | Wakefield et al. ............ | 514/267 |
| 2005/0065178 A1 | 3/2005 | Basha et al. | |
| 2006/0035936 A1 | 2/2006 | Buckley et al. | |
| 2008/0194577 A1 * | 8/2008 | Cai et al. .................. | 514/252.14 |

FOREIGN PATENT DOCUMENTS

| | | |
|---|---|---|
| JP | 6345642 A | 12/1994 |
| WO | WO9639407 A1 | 12/1996 |
| WO | WO9940070 | 8/1999 |
| WO | WO02064212 A1 | 8/2002 |
| WO | WO2005080348 A1 | 9/2005 |
| WO | WO2005110410 A2 | 11/2005 |
| WO | WO2005116009 A1 | 12/2005 |
| WO | WO 2006016014 A1 * | 2/2006 |
| WO | WO 2007022380 A2 * | 2/2007 |
| WO | WO2007030061 A1 | 3/2007 |
| WO | WO2008020405 A2 | 2/2008 |
| WO | WO 2008089034 A2 * | 7/2008 |

OTHER PUBLICATIONS

B Testa et al., Prodrug Design in, 5 Encyclopedia of Pharmaceutical Technology, 3008-3014 (J. Swarbrick ed., 3rd ed., 2007).*
J.H. Poupaert, Drug Design: Basic Principles and Applications, in 2 Encyclopedia of Pharmaceutical Technology 1362-1369, 1367 (James Swarbrick ed., 3rd ed., 2007).*
B.A. Chabner et al., Chemotherapy of Neoplastic Diseases, Neoplastic Agents in, Goodman & Gilman's: The Pharmacological Basis of Therapeutics 1315-1403, 1315 (L.L. Brunton et al., eds., 11th ed., 2006).*
R.R. Adams et al., 67 Journal of the American Chemical Society, 1159-1161 (1945).*
R. Ashworth et al., Journal of the Chemical Society 581-586 (1948).*
R. Hull et al., Journal of the Chemical Society 41-52 (1947).*
E.F. DiMauro et al., Journal of Medicinal Chemistry (2008), 51(6), 1681-1694.*
Arrang, et al., "Auto-inhibition of Brain Histamine Release Mediated by a Novel Class ($H_3$) of Histamine Receptor," Nature, 1983, vol. 302, pp. 832-837.
Arrang, et al., "Highly Potent and Selective Ligands for Histamine $H_3$-Receptors," Nature, 1987, vol. 327, pp. 117-123.
Arrang, et al., "Histamine $H_3$ Receptor Binding Sites in Rat Brain Membranes: Modulations by Guanine Nucleotides and Divalent Cations," European Journal of Pharmacology, 1990, vol. 188, pp. 219-227.
Barocelli, et al., "R-α-methyl Histamine-Induced Inhibition of Gastric Acid Secretion in Pylorus-ligated Rats Via Central Histamine $H_3$ Receptors," British Journal of Pharmacology, 1995, vol. 115 (7), pp. 1326-1330.
Bertaccini, et al., "An Update on Histamine $H_3$ Receptors and Gastrointestinal Functions," Digestive Diseases and Sciences, 1995, vol. 40 (9), pp. 2052-2063.
Bongers, et al., "The Akt/GSK-3 β Axis as a New Signaling Pathway of the Histamine $H_3$ Receptor," Journal of Neurochemistry, 2007, vol. 103 (1), pp. 248-258.
Brown, et al., "The Physiology of Brain Histamine," Progress in Neurobiology, 2001, vol. 63 (6), pp. 637-672.
Cannon, et al., "Activation of Peripheral and Spinal Histamine $H_3$ Receptors Inhibits Formalin-induced Inflammation and Nociception, Respectively," Pharmacology, Biochemistry and Behavior, 2007, vol. 88 (1), pp. 122-129.
Cannon, et al., "Activation of Spinal Histamine $H_3$ Receptors Inhibits Mechanical Nociception," European Journal of Pharmacology, 2003, vol. 470 (3), pp. 139-147.

(Continued)

*Primary Examiner* — Deepak Rao
*Assistant Examiner* — Alexander R Pagano
(74) *Attorney, Agent, or Firm* — Lisa V. Mueller; Michael Best & Friedrich LLP

(57) ABSTRACT

Compounds of the formula

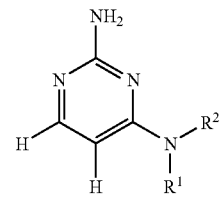

wherein $R^1$ and $R^2$ are as disclosed herein, are useful in treating conditions or disorders prevented by or ameliorated by histamine-3 receptor full or partial agonists. Also disclosed are pharmaceutical compositions, methods for using such compounds and compositions, and processes for preparing the compounds.

3 Claims, 1 Drawing Sheet

(56) References Cited

OTHER PUBLICATIONS

Cannon, et al., "Inhibition of Chemical and Low-Intensity Mechanical Nociception by Activation of Histamine $H_3$ Receptors," Journal of Pain, 2005, vol. 6 (3), pp. 193-200.

Cheng, et al., "Relationship Between the Inhibition Constant ($K_1$) and the Concentration of Inhibitor Which Causes 50 Per Cent Inhibition ($I_{50}$) of An Enzymatic Reaction," Biochemical Pharmacology, 1973, vol. 22, pp. 3099-3108.

Cross, et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.

Esbenshade, et al., "Pharmacological and Behavioral Properties of A-349821, a Selective and Potent Human Histamine $H_3$ Receptor Antagonist," Biochemical Pharmacology, 2004, vol. 68 (5), pp. 933-945.

Esbenshade, et al., "Pharmacological Properties of ABT-239 [4-(2-{2-[(2R)-2-Methylpyrrolidinyl]ethyl}-benzofuran-5-yl)benzonitrile]: I. Potent and Selective Histamine $H_3$ Receptor Antagonist with Drug-Like Properties," Journal of Pharmacology and Experimental Therapeutics, 2005, vol. 313 (1), pp. 165-175.

Esbenshade, et al., "Two Novel and Selective Nonimidazole Histamine $H_3$ Receptor Antagonists A-304121 and A-317920: I. In Vitro Pharmacological Effects," Journal of Pharmacology and Experimental Therapeutics, 2003, vol. 305 (3), pp. 887-896.

Fox, et al., "Differential in Vivo Effects of $H_3$ Receptor Ligands in a New Mouse Dipsogenia Model," Pharmacology Biochemistry and Behavior, 2002, vol. 72 (3), pp. 741-750.

Francis, et al., "$H_3$ Histamine Receptor Agonist Inhibits Biliary Growth of BDL Rats by Downregulation of the cAMP-Dependent PKA/ERK1/2/ELK-1 Pathway," Laboratory Investigation, 2007, vol. 87 (5), pp. 473-487.

Furniss, et al., Vogel's Textbook of Practical Organic Chemistry, 5th Edition, Longman Scientific & Technical, 1989, Table of Contents.

Ganellin, et al., "Synthesis of Potent Non-imidazole Histamine $H_3$-Receptor Antagonists," Archiv Der Pharmazie, 1998, vol. 331 (12), pp. 395-404.

Garbarg, et al., "S-[2-(4-Imidazolyl)ethyl]Isothiourea, a Highly Specific and Potent Histamine $H_3$ Receptor Agonist," Journal of Pharmacology and Experimental Therapeutics, 1992, vol. 263 (1), pp. 304-310.

Gothert, et al., "New Aspects of the Role of Histamine in Cardiovascular Function: Identification, Characterization, and Potential Pathophysiological Importance of $H_3$ Receptors," Canadian Journal of Physiology and Pharmacology, 1995, vol. 73 (5), pp. 558-564.

Harper, et al., "Characterization of the Binding of [$^3$H]-Clobenpropit to Histamine $H_3$-Receptors in Guinea-Pig Cerebral Cortex Membranes," British Journal of Pharmacology, 1999, vol. 128 (4), pp. 881-890.

Harusawa, et al., "Synthesis of Imifuramine and Its Stereoisomers Exhibiting Histamine $H_3$-Agonistic Activity," Tetrahedron Letters, 1999, vol. 40, pp. 2561-2564.

Kitbunnadaj, et al., "Identification of 4-(1H-Imidazol-4(5)-ylmethyl)pyridine (Immethridine) as a Novel, Potent, and Highly Selective Histamine $H_3$ Receptor Agonist," Journal of Medicinal Chemistry, 2004, vol. 47 (10), pp. 2414-2417.

Koyama, et al., "Increased Severity of Reperfusion Arrhythmias in Mouse Hearts Lacking Histamine $H_3$-Receptors," Biochemical and Biophysical Research Communications, 2003, vol. 306 (3), pp. 792-796.

Koyama, et al., "Norepinephrine Release from the Ischemic Heart Is Greatly Enhanced in Mice Lacking Histamine $H_3$ Receptors," Molecular Pharmacology, 2003, vol. 63 (2), pp. 378-382.

Krueger, et al., "G Protein-Dependent Pharmacology of Histamine $H_3$ Receptor Ligands: Evidence for Heterogeneous Active State Receptor Conformations," Journal of Pharmacology and Experimental Therapeutics, 2005, vol. 314 (1), pp. 271-281.

Kushida, et al., "PF1270A, B and C, Novel Histamine H3 Receptor Ligands Produced by *Penicillium waksmanii* PF1270," Journal of Antibiotics, 2007, vol. 60 (11), pp. 667-673.

Labella, et al., "$H_3$ Receptor Antagonist, Thioperamide, Inhibits Adrenal Steroidogenesis and Histamine Binding to Adrenocortical Microsomes and Binds to Cytochrome P450," British Journal of Pharmacology, 1992, vol. 107 (1), pp. 161-164.

Langford, et al., "Social Modulation of Pain as Evidence for Empathy in Mice," Science, 2006, vol. 312 (5782), pp. 1967-1970.

Lassen, et al., "Histamine-1 Receptor Blockade Does Not Prevent Nitroglycerin Induced Migraine," European Journal of Clinical Pharmacology, 1996, vol. 49 (5), pp. 335-339.

Leurs, et al., eds., "The Histamine $H_3$ Receptor: A Target for New Drugs," vol. 30, Elsevier Science B.V., 1998, Table of Contents.

Leurs, et al., "Histamine Homologues Discriminating between Two Functional $H_3$ Receptor Assays. Evidence for $H_3$ Receptor," Journal of Pharmacology and Experimental Therapeutics, 1996, vol. 276 (3), pp. 1009-1015.

Leurs, et al., "Therapeutic Potential of Histamine $H_3$ Receptor Agonists and Antagonists," Trends in Pharmacological Sciences, 1998, vol. 19 (5), pp. 177-183.

Levi, et al., "Histamine $H_3$-receptor signaling in cardiac sympathetic nerves: Identification of a novel MAPK-PLA$_2$-COX-PGE$_2$-EP$_3$R pathway", 2007, vol. 73(8), pp. 1146-1156.

Levi, et al., "Histamine $H_3$-Receptors: A New Frontier In Myocardial Ischemia," The Journal of Pharmacology And Experimental Therapeutics, 2000, vol. 292 (3), pp. 825-830.

Lin, et al., "Histaminergic Descending Inputs to the Mesopontine Tegmentum and their Role in the Control of Cortical Activation and Wakefulness in the Cat," Journal of Neuroscience, 1996, vol. 16 (4), pp. 1523-1537.

Lin, et al., "Involvement of Histaminergic Neurons in Arousal Mechanisms Demonstrated with $H_3$-Receptor Ligands in the Cat," Brain Research, 1990, vol. 523 (2), pp. 325-330.

Lipp, et al., "Synthesis, Absolute Configuration, Stereoselectivity, and Receptor Selectivity of (αR, βS)-,αβ-Dimethylhistamine, a Novel Highly Potent Histamine $H_3$ Receptor Agonist," Journal of Medicinal Chemistry, 1992, vol. 35 (23), pp. 4434-4441.

Lovenberg, et al., "Cloning and Functional Expression of the Human Histamine $H_3$ Receptor," Molecular Pharmacology, 1999, vol. 55 (6), pp. 1101-1107.

Ma, et al., "Synthesis and Antimicrobial Activity of 4H-4-Oxoquinolizine Derivatives: Consequences Of Structural Modification At The C-8 Position," Journal of Medicinal Chemistry, 1999, vol. 42 (20), pp. 4202-4213.

MacKins, et al., "Therapeutic Potential of $H_3$-Receptor Agonists in Myocardial Infarction," Expert Opinion on Investigational Drugs, 2000, vol. 9 (11), pp. 2537-2542.

Malinowska, "Histamine $H_3$ Receptors—General Characterization and their Functions in the Cardiovascular System", 1998, vol. 49, pp. 191-211.

Matsubara, et al., "UK-14,304, R(−)-α-Methyl-Histamine And SMS 201-995 Block Plasma Protein Leakage Within Dura Mater By Prejunctional Mechanisms," European Journal Of Pharmacology, 1992, vol. 224 (2-3), pp. 145-150.

McBriar, "Discovery of amide and heteroaryl isosteres as carbamate replacements in a series of orally active γ-secretase inhibitors", 2008, vol. 18 (1), pp. 215-219.

McLeod, et al., "Sch 50971, An Orally Active Histamine $H_3$ Inhibits Central Neurogenic Vascular Inflammation and Produces Sedation in the Guinea Pig," Journal of Pharmacology and Experimental Therapeutics, 1998, vol. 287 (1), pp. 43-50.

Monti, et al., "Sleep and Waking During Acute Histamine $H_3$ Agonist BP 2.94 or $H_3$ Antagonist Carboperamide (MR 16155) Administration in Rats," Neuropsychopharmacology, 1996, vol. 15 (1), pp. 31-35.

Monti, et al., "Effects of Selective Activation or Blockade of the Histamine $H_3$ Receptor on Sleep And Wakefulness," Journal of Pharmacology, 1991, vol. 205, pp. 283-287.

Monti, et al., "Involvement of Histamine in the Control of the Waking State," Journal of Life Sciences, 1993, vol. 53 (17), pp. 1331-1338.

Morini, et al., "(R)-Alpha Methylhistamine Inhibits Ethanol-Induced Gastric Lesions in the Rat: Involvement of Histamine $H_3$ Receptors," Digestion, 1995, vol. 56 (2), pp. 145-152.

(56) References Cited

OTHER PUBLICATIONS

Parmentier, et al., "The Brain $H_3$-Receptor as a Novel Therapeutic Target for Vigilance and Sleep-Wake Disorders," Biochemical Pharmacology, 2007, vol. 73 (8), pp. 1157-1171.
Poste, et al., "Lipid Vesicles as Carriers for Introducing Biologically Active Materials into Cells," Methods in Cell Biology, 1976, vol. 14, pp. 33-71.
Prinz, "Histamine Secretion From Rat Enterochromaffinlike Cells", 1993, vol. 105, pp. 449-461.
Rishton, "Nonleadlikeness and Leadlikeness in Biochemical Screening," Drug Discovery Today, 2003, vol. 8 (2), pp. 86-96.
Rouleau, et al., "Anti-Inflammatory and Antinociceptive Properties of BP 2-94, a Histamine $H_3$ Receptor Agonist Prodrug," Journal of Pharmacology and Experimental Therapeutics, 2000, vol. 295 (1), pp. 219-225.
Rouleau, et al., "Bioavailability, Antinociceptive and Antiflammatory Properties of BP 2-94, A Histamine $H_3$ Receptor Agonist Prodrug," The Journal of Pharmacology and Experimental Therapeutics, 1997, vol. 281 (3), pp. 1085-1094.
Sakai, et al., "Effects of Thioperamide, A Histamine $H_3$ Receptor Antagonist, On Locomotor Activity and Brain Histamine Content in Mast Cell-Deficient $WW/W^V$ Mice," Life Sciences, 1991, vol. 48 (25), pp. 2397-2404.
Seyedi, et al., "Histamine $H_3$-Receptor-Induced Attenuation of Norepinephrine Exocytosis: A Decreased Protein Kinase A Activity Mediates a Reduction in Intracellular Calcium", 2005, vol. 312(1), pp. 272-280.
Sherrill, et al., "The first synthesis of 1,5-diazacyclooctan-2-one and differentially protected 1,5-diazacyclooctanes", Tetrahedron Letters, 2007, vol. 48, pp. 7053-7056.
Shih, et al., "Trans-4-Methyl-3-Imidazoyl Pyrrolidine As A Potent, Highly Selective Histamine $H_3$ Receptor Agonist In Vivo," Bioorganic & Medicinal Chemistry Letters, 1998, vol. 8 (3), pp. 243-248.
Silver, et al., "Coupling of Histamine $H_3$ Receptors to Neuronal $Na^+/H^+$ Exchange: A Novel Protective Mechanism in Myocardial Ischemia," Proceedings of the National Academy of Sciences, 2001, vol. 98 (5), pp. 2855-2859.
Silver, et al., "Decreased Intracellular Calcium Mediates the Histamine $H_3$-Receptor-induced Attenuation of Norepinephrine Exocytosis From Cardiac Sympathetic Nerve Endings," Proceedings of the National Academy of Sciences, 2002, vol. 99 (1), pp. 501-506.
Soldani, "Modulation of Pentagastrin-Induced Histamine Release by Histamine $H_3$ Receptors in the Dog", 1996, vol. 31, pp. 631-638.
Tedford, "Pharmacological Characterization of GT-2016, A Non-Thiourea-Containing Histamine $H_3$ Antagonist: in Vitro and in Vivo Studies," The Journal of Pharmacology And Experimental Therapeutics, 1995, vol. 275 (2), pp. 598-604.
Vanni-Mercier, et al., "Waking Selective Neurons in the Posterior Hypothalamus and their Response to Histamine $H_3$ Receptor Ligands: An Electrophysiological Study in Freely Moving Cats," Behavioural Brain Research, 2003, vol. 144 (1-2), pp. 227-241.
Vollinga, et al., "A New Potent and Selective Histamine $H_3$ Receptor Agonist, 4-1H-Imidazol-4-ylmethyl)piperidine," Journal of Medicinal Chemistry, 1994, vol. 37 (3), pp. 332-333.
Yang, et al., "Coordination of Histamine $H_3$ Receptor Antagonists with Human Adrenal Cytochrome P450 Enzymes," Pharmacology, 2002, vol. 66 (3), pp. 128-135.
Yoshimoto, et al., "Therapeutic Potential of Histamine H3 Receptor Agonist for the Treatment of Obesity and Diabetes Mellitus," Proceedings of the National Academy of Sciences, 2006, vol. 103 (37), pp. 13866-13871.

* cited by examiner

Figure 1. Average 1-4 Hz slow wave EEG amplitude. 0-2 hours after injection of Example 1
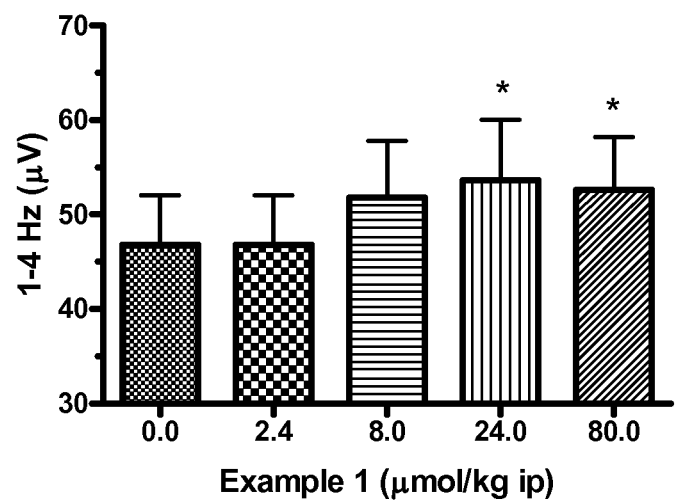
p= 0.0038 one-way repeated measures ANOVA
* p<0.05 Newman Keuls post-test

4-SUBSTITUTED-2-AMINO-PYRIMIDINE DERIVATIVES

CROSS-REFERENCE TO RELATED APPLICATION

This application claims the benefit of U.S. Provisional Patent Application No. 61/221,555, filed on Jun. 30, 2009, which is herein incorporated by reference in its entirety.

STATEMENT REGARDING FEDERALLY SPONSORED RESEARCH OR DEVELOPMENT

Not applicable.

BACKGROUND OF THE INVENTION

1. Technical Field

The invention relates to 4-substituted-2-amino-pyrimidine compounds, compositions comprising such compounds, methods for making the compounds, and methods of treating conditions and disorders using such compounds and compositions.

2. Description of Related Technology

Histamine is a well-known modulator of neuronal activity. At least four types of histamine receptors have been reported in the literature, typically referred to as histamine-1, histamine-2, histamine-3, and histamine-4. The class of histamine receptor known as histamine-3 receptors is believed to play a role in neurotransmission in the central nervous system.

The histamine-3 ($H_3$) receptor was first characterized pharmacologically on histaminergic nerve terminals (*Nature* 1983, 302, 832-837), where it regulates the release of neurotransmitters in both the central nervous system and peripheral organs, particularly the lungs, cardiovascular system and gastrointestinal tract. $H_3$ receptors are thought to be disposed presynaptically on histaminergic nerve endings, and also on neurons possessing other activity, such as adrenergic, cholinergic, serotoninergic, and dopaminergic activity. The existence of $H_3$ receptors has been confirmed by the development of selective $H_3$ receptor agonists and antagonists (*Nature* 1987, 327, 117-123; Leurs and Timmerman, ed. "*The History of $H_3$ Receptor: a Target for New Drugs*," Elsevier, 1998). The activity at the $H_3$ receptors can be modified or regulated by the administration of $H_3$ receptor ligands. The ligands can demonstrate agonist, partial agonist, antagonist, or inverse agonist activity. Activation of presynaptic $H_3$ receptors by full or partial agonists suppresses the release of the neurotransmitter associated with these neurons. Conversely, blockade of presynaptic $H_3$ receptors by antagonists or inverse agonists enhances the release of the neurotransmitter associated with these neurons.

Therapeutic potential for $H_3$ receptor agonists has been proposed for conditions and disorders related to a) neurological processes, such as sleep disorders (*Neuropsychopharmacology* 1996, 15(1), 31-35), migraine (*European Journal of Pharmacology* 1992, 224, 145-150), pain (*Journal of Pharmacology and Experimental Therapeutics* 2000, 295, 219-225), and Alzheimer's disease (*Journal of Neurochemistry* 2007, 103(1), 248-258); b) cardiovascular function, such as arrhythmias and myocardial infarction (WO2002/064212A1); c) inflammatory processes, such as edema, plasma protein extravasation, and polymorphonuclear leukocyte infiltration (*Journal of Pharmacology and Experimental Therapeutics* 2000, 295, 219-225); and d) gastrointestinal function, such as gastric acid related diseases (*Digestive Diseases and Sciences* 1995, 40(9), 2052-2063).

Several $H_3$ receptor agonists have been reported, such as R-alpha-methyl-histamine (*Nature* 1987, 327, 117-123), R-alpha-S-beta-dimethyl-histamine (*Journal of Medicinal Chemistry* 1992, 35(23), 4434-4441), imetit (*Journal of Pharmacology and Experimental Therapeutics* 1992, 263, 304-310), immepip (*Journal of Medicinal Chemistry* 1994, 37(3), 332-333), Sch-50971 (*Bioorganic & Medicinal Chemistry Letters* 1998, 8, 243-248), imifuramine (*Tetrahedron Letters* 1999, 40, 2561-2564), and immethridine (*Journal of Medicinal Chemistry* 2004, 47(10), 2414-2417), however, all of these compounds contain an imidazole ring in their structures. Imidazole moieties have been reported to impair the drug-likeness of compounds. Imidazole-containing $H_3$ ligands have been reported to have poor ability to access the central nervous system (CNS) (Ganellin, et al. *Arch. Pharm. Pharm. Med. Chem.* 1998, page 395). Since $H_3$ receptors are predominantly found in the CNS and the diseases targeted for treatment are modulated by neuronal tissues, it would be beneficial to provide non-imidazole containing CNS ligands. Compounds with imidazole moieties are usually potent inhibitors of liver enzymes, particularly the cytochrome $P_{450}$ enzymes that metabolize co-administered drugs. Literature reports of imidazole-containing $H_3$ ligands can be found in a) LaBella, F. S.; Queen, G.; Glavin, G.; Durant, G.; Stein, D.; Brandes, L. J. The $H_3$ antagonist thioperamide inhibits adrenal steroidogenesis and histamine binding to adrenocortical microsomes and inhibits cytochrome $P_{450}$. *Br. J. Pharmacol.* 1992, 107, 161-164, b) Yang, R.; Hey, J. A.; Aslanian, R.; Rizzo, C. A. Coordination of histamine $H_3$-receptor antagonists with human adrenal cytochrome $P_{450}$ enzymes. *Pharmacology* 2002, 66, 128-135, c) Harper, E. A.; Shankley, N. P.; Black, J. W. Characterization of the binding of [3H]-clobenpropit to histamine $H_3$-receptors in guinea pig cerebral cortex membranes. *Br. J. Pharmacol.* 1999, 128, 881-890.

An attempt to overcome some of the deficiencies of an imidazole-based $H_3$ receptor agonist is exemplified by BP 2-94, a benzophenone-imine prodrug of R-alpha-methyl-histamine (*Journal of Pharmacology and Experimental Therapeutics* 1997, 281, 1085-1094). Although this prodrug did address the rapid metabolism of R-alpha-methyl-histamine in humans and succeeded in providing significant levels in plasma and in peripheral tissues, it failed to deliver significant brain levels or address cytochrome $P_{450}$-based drug interactions.

Only a very few non-imidazole structures have ever been reported to be $H_3$ receptor agonists, such as three spiroindolinone natural products (*Journal of Antibiotics* 2007, 60(11), 667-673), however, these compounds lack good drug-like properties (Gilbert M. Rishton. Nonleadlikeness and lead-likeness in biochemical screening. *Drug Discovery Today* 2003, 8(2), 86) since their molecular weights are greater than 500 and they contain potential chemically reactive functional groups such as an ester, an aldehyde, and an epoxide. Another class of non-imidazole structures, derivatives of the sesquiterpene α-cedrene, have been described as $H_3$ receptor agonists (JP6345642A), however, the data described also reported that these have very low potency ($EC_{50}$>10 µM). It would be beneficial to provide additional non-imidazole compounds with improved drug-like properties and potency, demonstrating full or partial agonist activity at $H_3$ receptors that can be incorporated into pharmaceutical compositions useful for therapeutic methods.

BRIEF DESCRIPTION OF THE DRAWINGS

FIG. 1 is a graphical representation of slow wave electroencephalography (EEG) frequency when measured in male adult CD-1 rats of the Sprague-Dawley strain relative to the amount of a histamine-3 agonist, Example 1, administered.

SUMMARY OF THE INVENTION

The invention is directed to 4-substituted-2-amino-pyrimidine compounds and, more particularly, 4-substituted-2-amino-pyrimidines having a structure of formula (I):

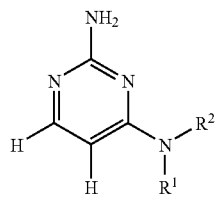

I or pharmaceutically acceptable salts thereof, wherein:
a) $R^1$ is hydrogen or methyl and
   $R^2$ is $-[C(R^3)(R^4)]_m-[C(R^5)(R^6)]_n-[C(R^7)(R^8)]_u-NR^AR^B$,
   wherein each occurrence of $R^3$, $R^4$, $R^5$, $R^6$, $R^7$, and $R^8$ are each independently hydrogen or lower alkyl, m is an integer from 1 to 4, n is an integer from 0 to 2, u is an integer from 0 to 1, $R^A$ is hydrogen, alkyl, arylalkyl, alkoxycarbonyl, or cycloalkyl, and $R^B$ is hydrogen or lower alkyl, or
b) $R^1$ is hydrogen or methyl and
   $R^2$ is $-[C(R^7)(R^8)]_u$-(Ring A), wherein $R^7$, $R^8$, and u are define as above, and Ring A is of the formula:

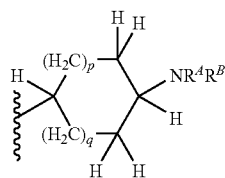

Ring A wherein $R^A$ and $R^B$ are as defined above, p is an integer from 0 to 2, and q is an integer from 0 to 2, or
c) $R^1$ is hydrogen or methyl, and
   $R^2$ is $-[C(R^7)(R^8)]_u$-(Ring B), wherein $R^7$, $R^8$, and u are defined as above, and Ring B is of the formula:

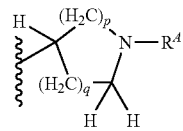

Ring B wherein $R^A$ is as defined above, p is an integer from 0 to 2, and q is an integer from 0 to 2, provided that p and u are not both equal to 0; or
d) $R^1$ and $R^2$ taken together with the nitrogen atom to which they are attached form Ring C of the formula:

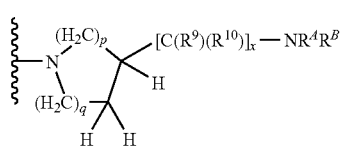

Ring C wherein $R^A$ and $R^B$ are defined as above, $R^9$ and $R^{10}$ are each independently hydrogen or lower alkyl; x is an integer from 0 to 2, p is an integer from 0 to 2, and q is an integer from 0 to 2, provided that p and x are not both equal to 0; or
e) $R^1$ and $R^2$ taken together with the nitrogen atom to which they are attached form Ring D of the formula:

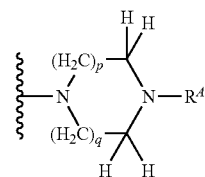

Ring D wherein $R^A$ is as defined above, p is an integer from 0 to 2, and q is an integer from 0 to 2, or
f) $R^1$ and $R^2$ taken together with the nitrogen atom to which they are attached form Ring E of the formula:

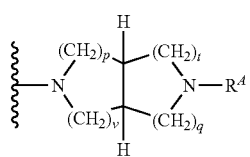

Ring E wherein $R^A$ is defined as above, p is an integer from 0 to 2, q is an integer from 0 to 2, v is an integer from 1 to 2, and t is an integer from 1 to 3, or
g) $R^1$ and $R^2$ taken together with the nitrogen atom to which they are attached form Ring F of the formula:

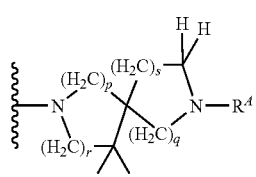

Ring F wherein $R^A$ is defined as above, r is an integer from 0 to 2, s is an integer from 0 to 2, p is an integer from 0 to 2, and q is an integer from 0 to 2, provided that p and q are not both equal to 0; and further provided that p is 1 or 2 when r is 0 and q is 1 or 2 when s is 0;
with the proviso that the compound is other than
   $N^4$-(5-(diethylamino)pentyl)pyrimidine-2,4-diamine,
   $N^4$-(5-aminopentyl)pyrimidine-2,4-diamine,
   $N^4$-(4-(diethylamino)butyl)pyrimidine-2,4-diamine,
   $N^4$-(3-(diethylamino)propyl)pyrimidine-2,4-diamine,
   $N^4$-(3-aminopropyl)pyrimidine-2,4-diamine, N⁴-(3-(dipropylamino)propyl)pyrimidine-2,4-diamine,
N⁴-(3-(dipentylamino)propyl)pyrimidine-2,4-diamine,
N⁴-(3-(diethylamino)propyl)-N⁴-methylpyrimidine-2,4-diamine,
N⁴-(6-(diethylamino)hexyl)pyrimidine-2,4-diamine,
N⁴-(6-aminohexyl)pyrimidine-2,4-diamine;
4-(piperazin-1-yl)pyrimidin-2-amine,
4-(4-methylpiperazin-1-yl)pyrimidin-2-amine,
4-(4-isopropylpiperazin-1-yl)pyrimidin-2-amine, or
4-(4-cyclopentyllpiperazin-1-yl)pyrimidin-2-amine.

Another aspect of the invention relates to pharmaceutical compositions comprising compounds of the invention or pharmaceutically acceptable salts or prodrugs thereof. Such compositions can be administered in accordance with a method of the invention, typically as part of a therapeutic regimen for treatment or prevention of conditions and disorders related to $H_3$ receptor activity.

Yet another aspect of the invention relates to a method of selectively modulating $H_3$ receptor activity. The method is useful for treating, or preventing conditions and disorders related to $H_3$ receptor modulation in mammals. More particularly, the method is useful for treating or preventing conditions and disorders related to sleep disorders. Accordingly, the compounds and compositions of the invention are useful as a medicament for treating or preventing $H_3$ receptor modulated disease, particularly, for treating or preventing sleep disorders.

Processes for making compounds of the invention also are contemplated.

The compounds, compositions comprising the compounds, methods for making the compounds, methods for treating or preventing conditions and disorders by administering the compounds, radiolabelled forms of the compounds, and compositions containing radiolabelled forms of the compounds are further described herein.

DETAILED DESCRIPTION OF THE INVENTION

Definition of Terms

Certain terms as used in the specification are intended to refer to the following definitions, as detailed below.

The term "acyl" as used herein means an alkyl group, as defined herein, appended to the parent molecular moiety through a carbonyl group, as defined herein. Representative examples of acyl include, but are not limited to, acetyl, 1-oxopropyl, 2,2-dimethyl-1-oxopropyl, 1-oxobutyl, and 1-oxopentyl.

The term "alkenyl" as used herein means a straight or branched chain hydrocarbon containing from 2 to 10 carbons, and preferably 2, 3, 4, 5, or 6 carbons, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy" as used herein means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxyimino" as used herein means an alkoxy group, as defined herein, appended to the parent molecular moiety through an imino group, as defined herein. Representative examples of alkoxyimino include, but are not limited to, ethoxy(imino)methyl and methoxy(imino)methyl.

The term "alkyl" as used herein means a straight or branched chain hydrocarbon containing from 1 to 10 carbon atoms, and preferably lower alkyl containing 1, 2, 3, 4, 5, or 6 carbons. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. Each of the carbon atoms of the alkyl group is substituted with hydrogen or with 0, 1, 2, or 3 substituents selected from hydroxy and halogen.

The term "alkylene" means a divalent group derived from a straight or branched chain hydrocarbon of from 1 to 10 carbon atoms. Representative examples of alkylene include, but are not limited to, —$CH_2$—, —$CH(CH_3)$—, —$C(CH_3)_2$—, —$CH_2CH_2$—, —$CH_2CH_2CH_2$—, —$CH_2CH_2CH_2CH_2$—, and —$CH_2CH(CH_3)CH_2$—.

The term "alkylamino" as used herein means an alkyl group, as defined herein, appended to the parent molecular moiety through a NH group. Representative examples of alkylamino include, but are not limited to, methylamino, ethylamino, isopropylamino, and butylamino.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl, ethylcarbonyl, isopropylcarbonyl, n-propylcarbonyl, and the like.

The term "alkylsulfonyl" as used herein means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylthio" as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkynyl" as used herein means a straight or branched chain hydrocarbon group containing from 2 to 10 carbon atoms, and preferably 2, 3, 4, or 5 carbons, and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amido" as used herein means an amino, alkylamino, or dialkylamino group appended to the parent molecular moiety through a carbonyl group, as defined herein. Representative examples of amido include, but are not limited to, aminocarbonyl, methylaminocarbonyl, dimethylaminocarbonyl, and ethylmethylaminocarbonyl.

The term "amino" as used herein means an —NH$_2$ group.

The term "aryl," as used herein, means phenyl, a bicyclic aryl, or a tricyclic aryl. The bicyclic aryl is attached to the parent molecular moiety through any carbon atom contained within the bicyclic aryl. Representative examples of the bicyclic aryl include, but are not limited to, dihydroindenyl, indenyl, naphthyl, dihydronaphthalenyl, and tetrahydronaphthalenyl. The tricyclic aryl is a tricyclic aryl ring system such as anthracene or phenanthrene, a bicyclic aryl fused to a cycloalkyl, a bicyclic aryl fused to a cycloalkenyl, or a bicyclic aryl fused to a phenyl. The tricyclic aryl is attached to the parent molecular moiety through any carbon atom contained within the tricyclic aryl. Representative examples of tricyclic aryl ring include, but are not limited to, anthracenyl, phenanthrenyl, azulenyl, dihydroanthracenyl, fluorenyl, and tetrahydrophenanthrenyl.

The term "arylalkyl" as used herein means an aryl group, as defined herein, appended to the parent molecular moiety through an alkyl group, as defined herein. Representative examples of arylalkyl include, but are not limited to, benzyl, 2-phenylethyl and 3-phenylpropyl.

The term "carbonyl" as used herein means a —C(=O)— group.

The term "cyano" as used herein means a —CN group, attached to the parent molecular moiety through the carbon.

The term "cycloalkyl" as used herein means a saturated cyclic hydrocarbon group containing from 3 to 8 carbons. Examples of cycloalkyl include cyclopropyl, cyclobutyl, cyclopentyl, cyclohexyl, cycloheptyl, and cyclooctyl.

The carbon atoms of the aryl groups and the cycloalkyl groups of this invention are substituted with hydrogen or are optionally substituted with one or more substituents ($R^{101}$) independently selected from acyl, alkenyl, alkoxy, alkoxyalkoxy, alkoxyalkyl, alkoxycarbonyl, alkoxyimino, alkyl, alkylcarbonyl, alkylsulfonyl, alkynyl, amido, carboxy, cyano, cycloalkyl, haloalkoxy, haloalkyl, halogen, hydroxy, hydroxyalkyl, and alkylthio. Where the aryl group is a phenyl group, the number of substituents is 0, 1, 2, 3, 4, or 5. Where the aryl group is a bicyclic aryl, the number of substituents is 0, 1, 2, 3, 4, 5, 6, 7, 8, or 9. Where the aryl group is a tricyclic aryl, the number of substituents is 0, 1, 2, 3, 4, 5, 6, 7, 8, or 9. The cycloalkyl groups of the invention may have up to 6 $R^{101}$ groups.

The term "dialkylamino" as used herein means two independent alkyl groups, as defined herein, appended to the parent molecular moiety through a nitrogen atom. Representative examples of dialkylamino include, but are not limited to, dimethylamino, diethylamino, ethylmethylamino, and butylmethylamino.

The term "halo" or "halogen" as used herein means Cl, Br, I, or F.

The term "haloalkoxy" as used herein means at least one halogen, as defined herein, appended to the parent molecular moiety through an alkoxy, as defined herein. Representative examples of haloalkoxy include, but are not limited to, 2-fluoroethoxy, trifluoromethoxy, and pentafluoroethoxy.

The term "haloalkyl" as used herein means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "hydroxy" as used herein means an —OH group.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "hydroxy-protecting group" means a substituent which protects hydroxyl groups against undesirable reactions during synthetic procedures. Examples of hydroxy-protecting groups include, but are not limited to, methoxymethyl, benzyloxymethyl, 2-methoxyethoxymethyl, 2-(trimethylsilyl)ethoxymethyl, benzyl, triphenylmethyl, 2,2,2-trichloroethyl, t-butyl, trimethylsilyl, t-butyldimethylsilyl, t-butyldiphenylsilyl, methylene acetal, acetonide benzylidene acetal, cyclic ortho esters, methoxymethylene, cyclic carbonates, and cyclic boronates. Hydroxy-protecting groups are appended onto hydroxy groups by reaction of the compound that contains the hydroxy group with a base, such as triethylamine, and a reagent selected from an alkyl halide, alkyl triflate, trialkylsilyl halide, trialkylsilyl triflate, aryldialkylsilyltriflate, or an alkylchloroformate, $CH_2I_2$, or a dihaloboronate ester, for example with methyliodide, benzyl iodide, triethylsilyltriflate, acetyl chloride, benzylchloride, or dimethylcarbonate. A protecting group also may be appended onto a hydroxy group by reaction of the compound that contains the hydroxy group with acid and an alkyl acetal.

The term "imino" as defined herein means a —C(=NH)— group.

The term "nitro" as used herein means a —NO$_2$ group.

The term "nitrogen protecting group" as used herein means those groups intended to protect a nitrogen atom against undesirable reactions during synthetic procedures. Nitrogen protecting groups comprise carbamates, amides, N-benzyl derivatives, and imine derivatives. Preferred nitrogen protecting groups are acetyl, benzoyl, benzyl, benzyloxycarbonyl (CBZ), formyl, phenylsulfonyl, pivaloyl, tert-butoxycarbonyl (Boc), tert-butylacetyl, trifluoroacetyl, and triphenylmethyl (trityl). Nitrogen-protecting groups are appended onto primary or secondary amino groups by reacting the compound that contains the amine group with base, such as triethylamine, and a reagent selected from an alkyl halide, an alkyl triflate, a dialkyl anhydride, for example as represented by an alkyl anhydride (alkyl-OC=O)$_2$O, a diaryl anhydride, for example as represented by (aryl-OC=O)$_2$O, an acyl halide, an alkylchloroformate, or an alkylsulfonylhalide, an arylsulfonylhalide, or halo-CON(alkyl)$_2$, for example acetylchloride, benzoylchloride, benzylbromide, benzyloxycarbonylchloride, formylfluoride, phenylsulfonylchloride, pivaloylchloride, (tert-butyl-O—C=O)$_2$O, trifluoroacetic anhydride, and triphenylmethylchloride.

As used herein, the term "agonist" encompasses and describes compounds that activate H$_3$ receptors, such as histamine, with either full or partial efficacy.

Compounds of the Invention

Compounds of the invention can have the formula (I) as described in the Summary of the Invention.

One embodiment contemplated as part of the invention includes, but is not limited to, compounds of formula (II):

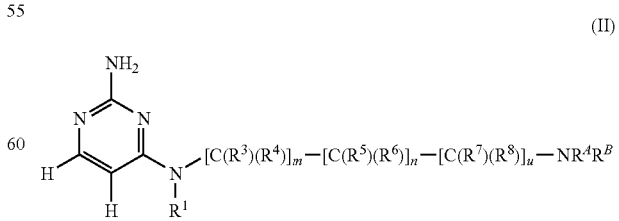

(II)

wherein $R^1$ is hydrogen or methyl, each occurrence of $R^3$, $R^4$, $R^5$, $R^6$, $R^7$, and $R^8$ are each independently hydrogen or lower alkyl, $R^A$ is hydrogen, alkyl, arylalkyl, alkoxycarbonyl, or cycloalkyl, $R^B$ is hydrogen or lower alkyl, m is an integer from 1 to 4, n is an integer from 0 to 2, and u is an integer from 0 to 1.

Certain embodiments of compounds of formula (II) include, but are not limited to, those wherein $R^1$ is hydrogen or methyl.

Certain embodiments of compounds of formula (II) include, but are not limited to, those wherein $R^3$ and $R^4$ can be the same or different, and each occurrence of $R^3$ and $R^4$ are independently hydrogen, methyl or ethyl.

Certain embodiments of compounds of formula (II) include, but are not limited to, those wherein $R^A$ is hydrogen or methyl, and $R^B$ is hydrogen or methyl.

Another embodiment contemplated as part of the invention includes, but is not limited to, compounds of formula (III):

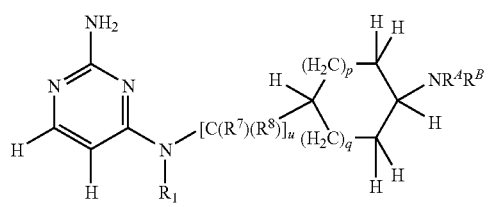

(III)

wherein $R^1$ is hydrogen or methyl, $R^7$ and $R^8$ are each independently hydrogen or lower alkyl, $R_A$ is hydrogen, alkyl, arylalkyl, alkoxycarbonyl, or cycloalkyl, $R^B$ is hydrogen or lower alkyl; u is an integer from 0 to 1, p is an integer from 0 to 2, and q is an integer from 0 to 2.

Certain embodiments of compounds of formula (III) include, but are not limited to, those wherein $R^1$ is hydrogen.

Certain embodiments of compounds of formula (III) include, but are not limited to, those wherein u is 0.

Certain embodiments of compounds of formula (III) include, but are not limited to, those wherein $R^7$ and $R^8$ are hydrogen when u is 1.

Certain embodiments of compounds of formula (III) include, but are not limited to, those wherein $R^A$ and $R^B$ are hydrogen.

Another embodiment contemplated as part of the invention includes, but is not limited to, compounds of formula (IV):

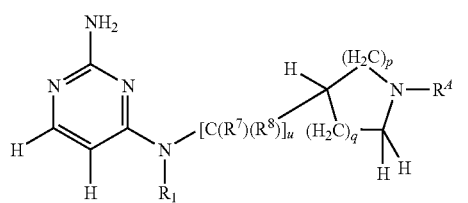

(IV)

wherein $R^1$ is hydrogen or methyl, $R^7$ and $R^8$ are each independently hydrogen or lower alkyl, $R^A$ is hydrogen, alkyl, arylalkyl, alkoxycarbonyl, or cycloalkyl, u is an integer from 0 to 1, p is an integer from 0 to 2, and q is an integer from 0 to 2, provided that p and u are not both equal to 0.

Certain compounds of formula (IV) include, but are not limited to, those wherein $R^1$ is hydrogen.

Certain embodiments of compounds of formula (IV) include, but are not limited to, those wherein u is 0.

Certain embodiments of compounds of formula (IV) include, but are not limited to, those wherein $R^7$ and $R^8$ are hydrogen when u is 1.

Certain embodiments of compounds of formula (IV) include, but are not limited to, those wherein $R^A$ is hydrogen, arylalkyl (for example, benzyl), or alkoxycarbonyl (e.g. tert-butoxycarbonyl).

Another embodiment contemplated as part of the invention includes, but is not limited to, compounds of formula (V):

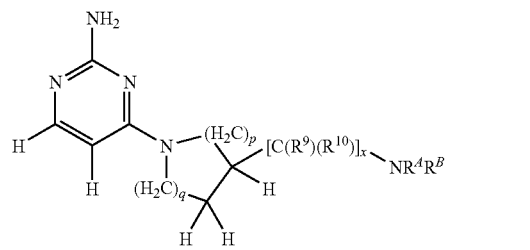

(V)

wherein $R^9$, $R^{10}$ are each independently hydrogen or lower alkyl; $R^A$ is hydrogen, alkyl, arylalkyl, alkoxycarbonyl, or cycloalkyl, $R^B$ is hydrogen or lower alkyl, p is an integer from 0 to 2, q is an integer from 0 to 2; x is an integer from 0 to 2, provided that p and x are not both equal to 0.

Certain embodiments of compounds of formula (V) include, but are not limited to, those wherein $R^9$ and $R^{10}$ are hydrogen when x is 1 or 2.

Certain embodiments of compounds of formula (V) include, but are not limited to, those wherein x is 0 or 1.

Certain embodiments of compounds of formula (V) include, but are not limited to, those wherein $R^A$ and $R^B$ are hydrogen.

Another embodiment contemplated as part of the invention includes, but is not limited to, compounds of formula (VI):

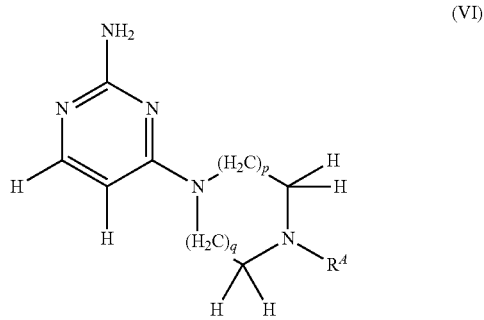

(VI)

wherein $R^A$ is hydrogen, alkyl, arylalkyl, alkoxycarbonyl, or cycloalkyl; p is an integer from 0 to 2, and q is an integer from 0 to 2.

Examples of compounds of formula (VI) include, but are not limited to, those wherein $R^A$ is hydrogen, alkyl (e.g. methyl), alkoxycarbonyl (e.g. tert-butoxycarbonyl), or arylalkyl (e.g. benzyl).

Another embodiment contemplated as part of the invention includes, but is not limited to, compounds of formula (VII):

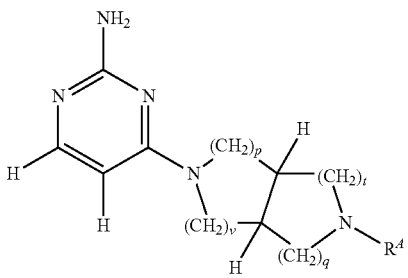

(VII)

wherein $R^A$ is hydrogen, alkyl, arylalkyl, alkoxycarbonyl, or cycloalkyl, p is an integer from 0 to 2, q is an integer from 0 to 2, v is an integer from 1 to 2, and t is an integer from 1 to 3.

Examples of compounds of formula (VII) include, but are not limited to, those wherein $R^A$ is hydrogen or arylalkyl (e.g. benzyl).

Another embodiment contemplated as part of the invention includes, but is not limited to, compounds of formula (VIII):

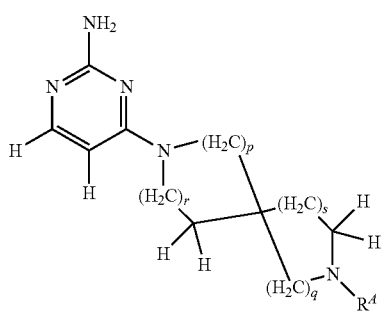

(VIII)

wherein $R^A$ is hydrogen, alkyl, arylalkyl, alkoxycarbonyl or cycloalkyl, p is an integer from 0 to 2, q is an integer from 0 to 2, r is an integer from 0 to 2, and s is an integer from 0 to 2, provided that p and q are not both equal to 0, and further provided that p is 1 or 2 when r is 0 and q is 1 or 2 when s is 0.

Examples of compounds of formula (VIII) include, but are not limited to, those wherein $R^A$ is hydrogen.

Specific embodiments contemplated as part of the invention also include, but are not limited to, compounds selected from the group consisting of:

$N^4$-(2-aminoethyl)pyrimidine-2,4-diamine;
$N^4$-(2-(dimethylamino)ethyl)pyrimidine-2,4-diamine;
$N^4$-(2-(dimethylamino)ethyl)-$N^4$-methylpyrimidine-2,4-diamine;
$N^4$-(2-aminopropyl)pyrimidine-2,4-diamine;
$N^4$-(1-aminopropan-2-yl)pyrimidine-2,4-diamine;
$N^4$-(2-amino-2-methylpropyl)pyrimidine-2,4-diamine;
$N^4$-(1-amino-2-methylpropan-2-yl)pyrimidine-2,4-diamine;
$N^4$-(3-aminopropyl)pyrimidine-2,4-diamine;
$N^4$-(3-(methylamino)propyl)pyrimidine-2,4-diamine;
$N^4$-(3-aminopropyl)-$N^4$-methylpyrimidine-2,4-diamine;
$N^4$-(3-(dimethylamino)propyl)-$N^4$-methylpyrimidine-2,4-diamine;
$N^4$-(3-aminopentyl)pyrimidine-2,4-diamine;
$N^4$-(1-aminopentan-3-yl)pyrimidine-2,4-diamine;
$N^4$-(3-amino-2,2-dimethylpropyl)pyrimidine-2,4-diamine;
$N^4$-(1-benzylpiperidin-4-yl)pyrimidine-2,4-diamine;
4-(4-methylpiperazin-1-yl)pyrimidin-2-amine;
tert-butyl 4-(2-aminopyrimidin-4-yl)piperazine-1-carboxylate;
tert-butyl 4-((2-aminopyrimidin-4-ylamino)methyl)piperidine-1-carboxylate;
trans-$N^4$-(4-aminocyclohexyl)pyrimidine-2,4-diamine;
(R)-tert-butyl 3-(2-aminopyrimidin-4-ylamino)pyrrolidine-1-carboxylate;
(R)—$N^4$-(pyrrolidin-3-yl)pyrimidine-2,4-diamine;
(3aR,6aS)-tert-butyl 5-(2-aminopyrimidin-4-yl)hexahydropyrrolo[3,4-c]pyrrole-2(1H)-carboxylate;
4-(4-aminopiperidin-1-yl)pyrimidin-2-amine;
4-(5-benzyl-1,5-diazocan-1-yl)pyrimidin-2-amine;
$N^4$-(azetidin-3-yl)pyrimidine-2,4-diamine;
4-(2,7-diazaspiro[3.5]nonan-7-yl)pyrimidin-2-amine;
$N^4$-(piperidin-4-yl)pyrimidine-2,4-diamine; and
4-(piperazin-1-yl)pyrimidin-2-amine.

Preferred compounds include at least:
$N^4$-(2-aminoethyl)pyrimidine-2,4-diamine;
$N^4$-(3-aminopropyl)pyrimidine-2,4-diamine;
4-(4-methylpiperazin-1-yl)pyrimidin-2-amine;
$N^4$-(azetidin-3-yl)pyrimidine-2,4-diamine;
4-(2,7-diazaspiro[3.5]nonan-7-yl)pyrimidin-2-amine; and
4-(piperazin-1-yl)pyrimidin-2-amine.

Compound names are assigned by using AUTONOM naming software, which is provided by MDL Information Systems GmbH (formerly known as Beilstein Informationssysteme) of Frankfurt, Germany, and is part of the CHEMDRAW® ULTRA v. 6.0.2 software suite.

Compounds of the invention may exist as stereoisomers when asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutanes may be present in the cis or trans configuration, and may be present as a single isomer or a mixture of the cis and trans isomers. Individual cis or trans isomers of compounds of the invention may be prepared synthetically from commercially available starting materials using selective organic transformations, or by prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention. It is also understood that the compounds of the invention may exist as isotopomers, wherein atoms may have different weights; for example, hydrogen and deuterium, or $^{12}C$ and $^{13}C$.

Methods for Preparing Compounds of the Invention

The compounds of the invention can be better understood in connection with the following synthetic schemes and methods which illustrate a means by which the compounds can be prepared.

Abbreviations which have been used in the descriptions of the schemes and the examples that follow are: DCM for dichloromethane, DIEA for diisopropylethylamine (Hunig's base), DMF for N,N-dimethylformamide; BINAP for 2,2'-bis(diphenylphosphino)-1,1'-binaphthyl; Bn for benzyl; Boc for butyloxycarbonyl; Et for ethyl; EtOAc for ethyl acetate; Et$_2$O for diethyl ether; HPLC for high pressure liquid chromatography; IPA for isopropyl alcohol; Me for methyl; MeOH for methanol; MgSO$_4$ for magnesium sulfate; Ms for methanesulfonyl; NH$_3$ for ammonia; Pd for palladium; tBu for tert-butyl; TEA for triethylamine; TFA for trifluoroacetic acid; THF for tetrahydrofuran; and Ts for para-toluenesulfonyl; rt for "room temperature" or ambient temperature suitably ranging 20-30° C. Microwave heating was accomplished in a commercial microwave apparatus.

The compounds of this invention can be prepared by a variety of synthetic procedures. Representative procedures are shown in, but are not limited to, Schemes 1-2.

Scheme 1

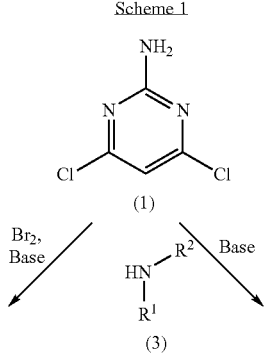

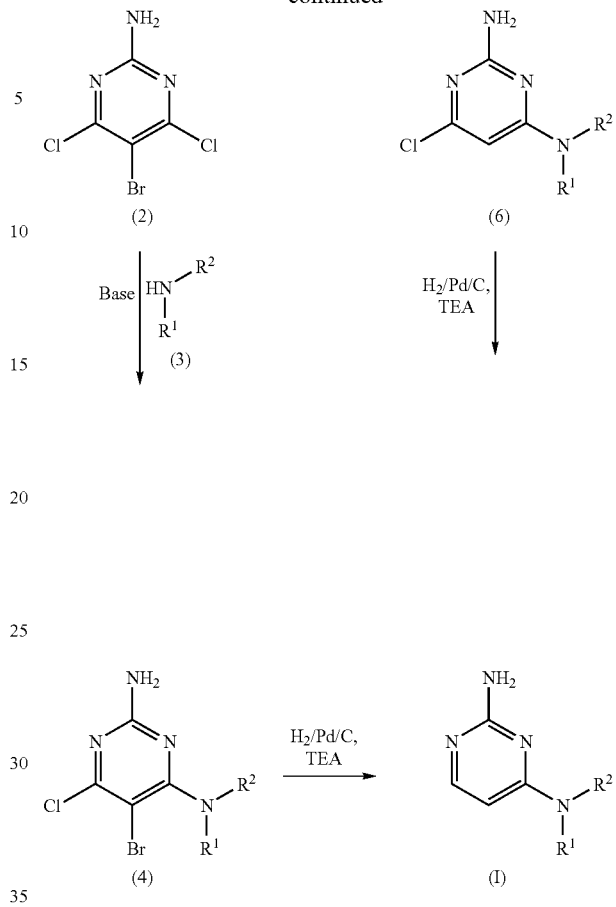

Compounds of general formula (I) can be prepared from the commercially available 4,6-dichloropyrimidin-2-amine (formula (1), CAS#56-05-3) by two distinct approaches as described in Scheme 1, wherein NR$^1$R$^2$ is as defined in formula (I). In the first approach, the compound of formula (1) is brominated in the 5-position with bromine in the presence of a base such as sodium carbonate in an aqueous alcohol solvent system such as 1:1 water/ethanol. The brominated intermediate of formula (2) is activated towards facile reaction with the diamine compounds of formula (3) in the presence of a base such as triethylamine or Hunig's base in a polar, aprotic solvent such as DMF, DMSO, or acetonitrile to form compounds of formula (4). The compounds of formula (4) can be dehalogenated by reaction with hydrogen gas in the presence of palladium on charcoal and a base such as triethylamine in a suitable solvent system such as methanol/ethyl acetate or ethanol/ethyl acetate to provide compounds of general formula (I).

A second approach involves direct reaction of the compound of formula (1) with the diamine compounds of formula (3) in the presence of a base such as triethylamine or Hunig's base under more forcing conditions such as heating in a sealed tube in solvents such as ethanol, n-propanol, i-propanol, or n-butanol to yield intermediates of formula (6). The intermediates of formula (6) may then be dechlorinated by reaction with hydrogen gas in the presence of palladium on charcoal and a base such as triethylamine in a suitable solvent system such as methanol/ethyl acetate or ethanol/ethyl acetate to provide compounds of general formula (I).

There are many suitable and readily available diamines of formula (3). Examples of such diamines are exemplified, but not limited to, those shown in Table 1.

TABLE 1

Examples of readily available diamine starting materials (HNR$^1$R$^2$) of formula (3).

| Amines | Structures | Commercial Source, Chemical Abstracts Number (CAS #), or Literature Reference |
|---|---|---|
| tert-butyl 2-aminoethylcarbamate | 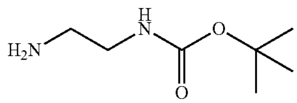 | CAS# 57260-73-8, Sigma-Aldrich PO Box 14508 St. Louis, MO, 63178 USA |
| N$^1$,N$^1$-dimethylethane-1,2-diamine | 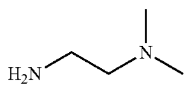 | CAS# 108-00-9, Sigma-Aldrich PO Box 14508 St. Louis, MO, 63178 |
| N$^1$,N$^1$,N$^2$-trimethylethane-1,2-diamine | 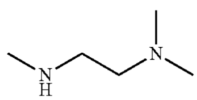 | CAS# 142-25-6, Sigma-Aldrich PO Box 14508 St. Louis, MO, 63178 |
| propane-1,2-diamine | 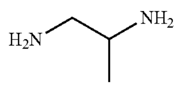 | CAS# 78-90-0, Sigma-Aldrich PO Box 14508 St. Louis, MO, 63178 |
| (S)-propane-1,2-diamine dihydrochloride | 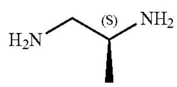 | CAS# 19777-66-3, Sigma-Aldrich PO Box 14508 St. Louis, MO, 63178 |
| (R)-propane-1,2-diamine dihydrochloride | 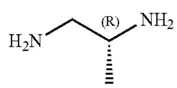 | CAS# 19777-67-4, Sigma-Aldrich PO Box 14508 St. Louis, MO, 63178 |
| 2-methylpropane-1,2-diamine | 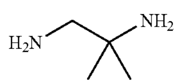 | CAS # 811-93-8, TCI America 9211 N. Harborgate St. Portland, OR, 97203 USA |
| tert-butyl 3-aminopropylcarbamate | 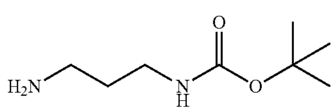 | CAS # 75178-96-0 Sigma-Aldrich PO Box 14508 St. Louis, MO, 63178 |
| pentane-1,3-diamine | 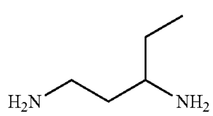 | CAS # 589-37-7, Sigma-Aldrich PO Box 14508 St. Louis, MO, 63178 |
| 2,2-dimethylpropane-1,3-diamine | 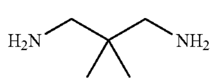 | CAS # 7328-91-8, Sigma-Aldrich PO Box 14508 St. Louis, MO, 63178 |
| 1-benzylpiperidin-4-amine | 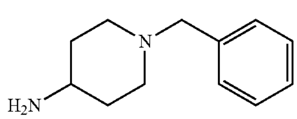 | CAS # 50541-93-0, Sigma-Aldrich PO Box 14508 St. Louis, MO, 63178 |
| 1-methylpiperazine | 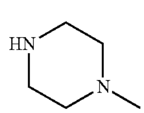 | CAS # 109-01-3, Sigma-Aldrich PO Box 14508 St. Louis, MO, 63178 |
| tert-butyl piperazine-1-carboxylate | 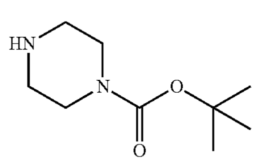 | CAS # 57260-71-6, Sigma-Aldrich PO Box 14508 St. Louis, MO, 63178 |

TABLE 1-continued

Examples of readily available diamine starting materials (HNR$^1$R$^2$) of formula (3).

| Amines | Structures | Commercial Source, Chemical Abstracts Number (CAS #), or Literature Reference |
|---|---|---|
| tert-butyl 4-(aminomethyl)piperidine-1-carboxylate | 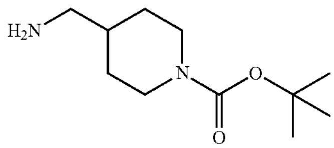 | CAS # 144222-22-0, Sigma-Aldrich PO Box 14508 St. Louis, MO, 63178 |
| (1r,4r)-cyclohexane-1,4-diamine | 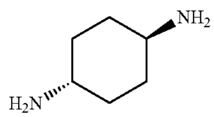 | CAS # 2615-25-0, Sigma-Aldrich PO Box 14508 St. Louis, MO, 63178 |
| (S)-tert-butyl 3-aminopyrrolidine-1-carboxylate | 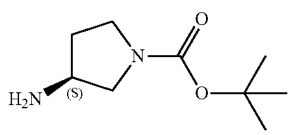 | CAS # 147081-44-5, Sigma-Aldrich PO Box 14508 St. Louis, MO, 63178 |
| (R)-tert-butyl 3-aminopyrrolidine-1-carboxylate | 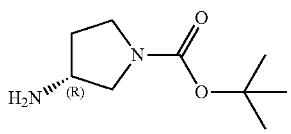 | CAS # 147081-49-0, Sigma-Aldrich PO Box 14508 St. Louis, MO, 63178 |
| (S)-tert-butyl pyrrolidin-3-ylcarbamate | 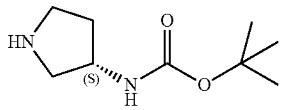 | CAS # 122536-76-9, Sigma-Aldrich PO Box 14508 St. Louis, MO, 63178 |
| (R)-tert-butyl pyrrolidin-3-ylcarbamate | 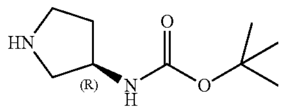 | CAS # 122536-77-0, Sigma-Aldrich PO Box 14508 St. Louis, MO, 63178 |
| (3aR,6aS)-tert-butyl hexahydropyrrolo[3,4-c]pyrrole-2(1H)-carboxylate | 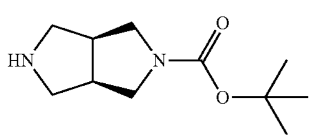 | CAS # 250275-15-1, Tyger Scientific Inc. 324 Stokes Avenue Ewing, NJ, 08638 USA |
| (3aR,6aS)-2-benzyloctahydropyrrolo[3,4-c]pyrrole | 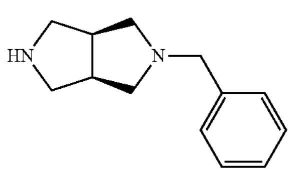 [SMILES: c1ccc(CN2C[C@H]3CNC[C@H]3C2)cc1] | CAS # 172739-04-7, Tyger Scientific Inc. 324 Stokes Avenue Ewing, NJ, 08638 |
| tert-butyl piperidin-4-ylcarbamate | 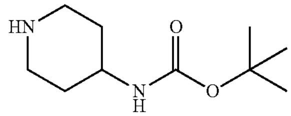 | CAS # 73874-95-0, Sigma-Aldrich PO Box 14508 St. Louis, MO, 63178 |
| tert-butyl 4-aminopiperidine-1-carboxylate | 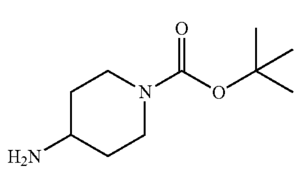 | CAS # 87120-72-7, Sigma-Aldrich PO Box 14508 St. Louis, MO, 63178 |

TABLE 1-continued

Examples of readily available diamine starting materials (HNR$^1$R$^2$) of formula (3).

| Amines | Structures | Commercial Source, Chemical Abstracts Number (CAS #), or Literature Reference |
|---|---|---|
| 1-benzyl-1,5-diazocane | 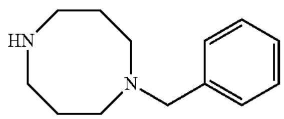 [SMILES: c1ccc(CN2CCCNCCC2)cc1] | CAS # 96097-97-1, Sherrill, R. G.; *Tetrahedron Letters* 2007, 48, 7053-7056 |
| tert-butyl 3-aminoazetidine-1-carboxylate | 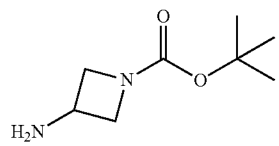 | CAS # 193269-78-2, Oakwood Products 1741 Old Dunbar Rd. West Columbia, SC, 29172 USA |
| tert-butyl azetidin-3-ylcarbamate | 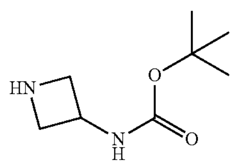 | CAS # 91188-13-5, Beta Pharma, Inc. 91 Shelton Avenue, Suite: 211 New Haven, CT, 06511 USA |
| tert-butyl 2,7-diazaspiro[3.5]nonane-2-carboxylate | 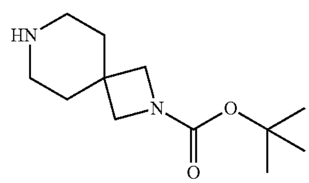 [SMILES: CC(C)(C)OC(=O)N1CC2(CCNCC2)C1] | CAS # 896464-16-7, WO2007/030061 A1 |
| tert-butyl 2,7-diazaspiro[3.5]nonane-7-carboxylate | 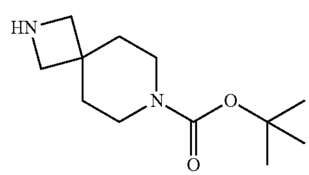 [SMILES: CC(C)(C)OC(=O)N1CCC2(CC1)CNC2] | CAS # 236406-55-6, WO2007/030061 A1 |
| tert-butyl 1,4-diazepane-1-carboxylate | 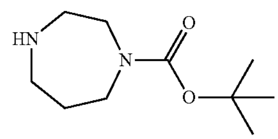 | CAS # 112275-50-0, Sigma-Aldrich PO Box 14508 St. Louis, MO, 63178 |
| tert-butyl 3,9-diazaspiro[5.5]undecane-3-carboxylate | 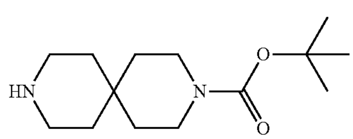 [SMILES: CC(C)(C)OC(=O)N1CCC2(CCNCC2)CC1] | CAS # 173405-78-2, Tyger Scientific Inc. 324 Stokes Avenue Ewing, NJ, 08638 |
| tert-butyl (1r,3r)-3-aminocyclobutylcarbamate | 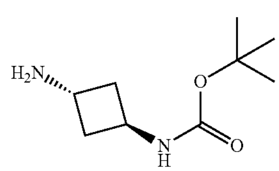 | CAS # 871014-19-6, WO2005/116009 A1 |
| tert-butyl (1s,3s)-3-aminocyclobutylcarbamate | 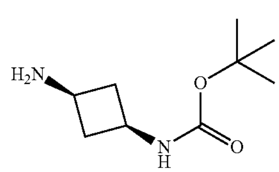 | WO2005/116009 A1 |

TABLE 1-continued

Examples of readily available diamine starting materials (HNR$^1$R$^2$) of formula (3).

| Amines | Structures | Commercial Source, Chemical Abstracts Number (CAS #), or Literature Reference |
|---|---|---|
| (1S,5S)-benzyl 3,6-diazabicyclo[3.2.0]heptane-3-carboxylate | 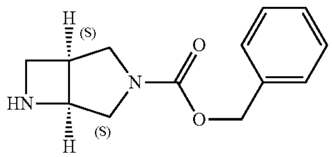 | CAS # 370881-43-9, US2006/035936 A1 |
| (1S,5R)-benzyl 3,6-diazabicyclo[3.2.0]heptane-3-carboxylate | 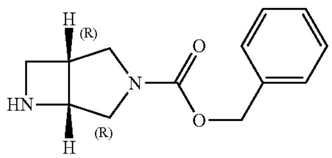 | CAS # 370881-68-8, US2005/065178 A1 |
| (1R,5S)-tert-butyl 3,6-diazabicyclo[3.2.0]heptane-6-carboxylate | 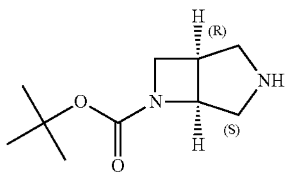 | CAS # 799279-81-5, US2006/035936 A1 |
| (1S,5R)-tert-butyl 3,6-diazabicyclo[3.2.0]heptane-6-carboxylate | 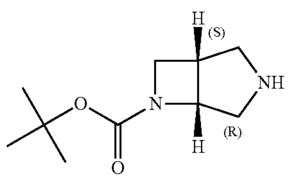 | CAS # 370882-66-9, US2005/065178 A1 |
| (3aR,7aR)-2-benzyloctahydro-1H-pyrrolo[3,4-c]pyridine | 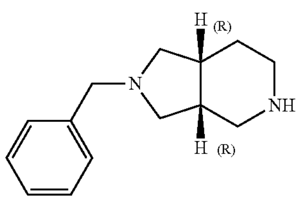 | CAS # 870237-33-5, WO2005/110410 A2 |
| (3aS,7aR)-5-benzyloctahydro-1H-pyrrolo[3,4-c]pyridine | 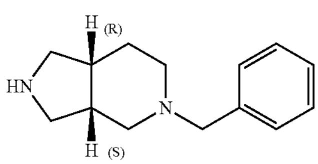 | CAS # 236406-57-8, WO1999/40070 A1 |
| (3aS,7aS)-5-benzyloctahydro-1H-pyrrolo[3,4-c]pyridine | 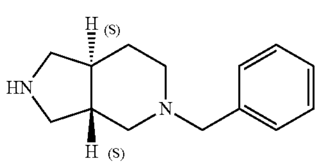 | CAS # 250275-17-3, Ma, Z.; et al.; *Journal of Medicinal Chemistry* 1999, 42(20), 4202-4213 |
| (4aS,7aS)-tert-butyl octahydro-1H-pyrrolo[3,4-b]pyridine-1-carboxylate | 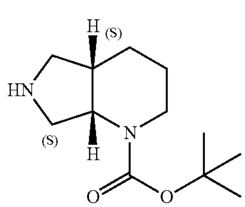 | CAS # 159991-07-8, WO1996/39407A1 |

TABLE 1-continued

Examples of readily available diamine starting materials (HNR$^1$R$^2$) of formula (3).

| Amines | Structures | Commercial Source, Chemical Abstracts Number (CAS #), or Literature Reference |
|---|---|---|
| (4aS,7aR)-tert-butyl octahydro-1H-pyrrolo[3,4-b]pyridine-1-carboxylate | 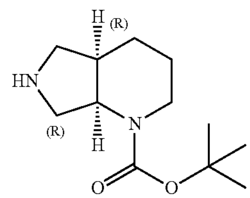 | CAS # 186201-89-8 WO1996/39407A1 |
| 1,7-diazaspiro[3.5]nonane | 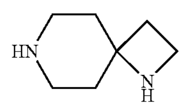 | CAS # 25408-26-8, McBriar, M. D.; et al.; *Bioorganic & Medicinal Chemistry Letters* 2008, 18(1), 215-219 |
| tert-butyl 3-(aminomethyl)azetidine-1-carboxylate | 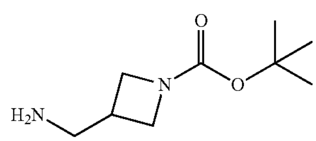 | CAS # 325775-44-8, AlfaAesar 26 Parkridge Road Ward Hill, MA 01835 USA |
| tert-butyl azetidin-3-ylmethylcarbamate | 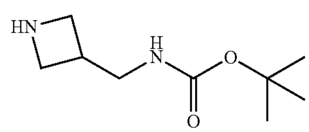 | CAS # 91188-15-7, Beta Pharma, Inc. 91 Shelton Avenue Suite 211 New Haven, CT 06511 USA |
| tert-butyl azetidin-2-ylmethylcarbamate | 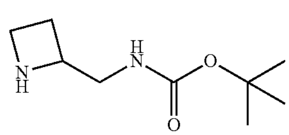 | CAS# 99724-21-7, Focus Synthesis LLC 10929 Technology Pl. Suite B San Diego, CA 92127 USA |
| (R)-tert-butyl 2-(aminomethyl)azetidine-1-carboxylate | 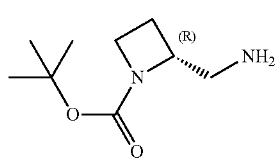 | CAS # 887626-82-6, WO2008/020405 A2 |
| (S)-tert-butyl 2-(aminomethyl)azetidine-1-carboxylate | 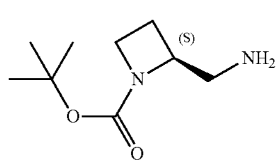 | CAS # 1007873-90-6, WO2008/020405 A2 |
| (3aS,8aS)-tert-butyl octahydropyrrolo[3,4-d]azepine-6(7H)-carboxylate | 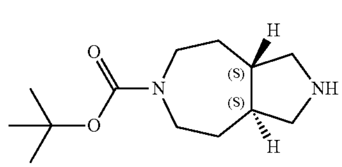 | CAS # 863222-24-6, WO2005/080348 A1 |

Alternatively, compounds of formula (I) may be prepared from the commercially available 4-chloropyrimidin-2-amine (formula (7), CAS#3993-78-0) as described in Scheme 2:

Scheme 2

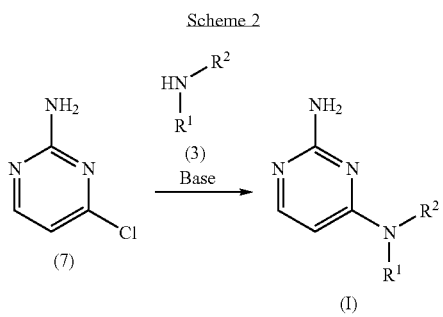

In this approach, reaction of the compound of formula (7) with the diamines of formula (3), either in the presence of a base such as triethylamine or Hunig's base or simply in the presence of excess diamines of formula (3) by heating in a sealed tube in solvents such as i-propanol or n-butanol provides compounds of formula (5).

The diamines of formula (3) used in Schemes 1 and 2 may be protected on one of the two nitrogen atoms with protecting groups such as Boc, CBZ, or benzyl. When the protecting group is benzyl or CBZ, it will remain intact in compounds of formula (I), and if desired, may be removed on treatment of compounds of formula (I) with hydrogen gas in the presence of palladium on charcoal in a suitable solvent such as methanol or ethanol to provide compounds of formula (I) in which the formerly protected nitrogen is converted to an NH or $NH_2$ group. When the protecting group is Boc, it will remain intact in compounds of formula (I), and if desired, may be removed on treatment of compounds of formula (I) with excess acid such as HCl or TFA in solvents such as methanol, ethanol, or dichloromethane to provide compounds of formula (I) in which the formerly protected nitrogen is converted to an NH or $NH_2$ group. Such primary or secondary amine containing compounds of formula (I) may be further substituted on nitrogen by reaction with an aldehyde or ketone in the presence of a reducing agent such as sodium triacetoxyborohydride or sodium cyanoborohydride.

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

The compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid (2,3-dihydroxy succinic acid), D(-)-tartaric acid, L(+)-tartaric acid, lactic acid, succinic acid, as well as mandelic, atrolactic, methane-sulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, or hydroxybutyric acid, camphorsulfonic, malic, phenylacetic, aspartic, glutamic, and the like.

Compositions of the Invention

The invention also provides pharmaceutical compositions comprising a therapeutically effective amount of a compound of formula (Ia)

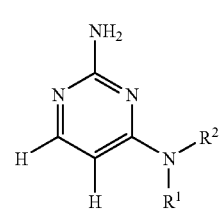

Ia or a pharmaceutically acceptable salt or prodrug thereof, wherein:
a) $R^1$ is hydrogen or methyl and
   $R^2$ is —$[C(R^3)(R^4)]_m$—$[C(R^5)(R^6)]_n$—$[C(R^7)(R^8)]_u$—$NR^AR^B$,
   wherein each occurrence of $R^3$, $R^4$, $R^5$, $R^6$, $R^7$, and $R^8$ are each independently hydrogen or lower alkyl, m is an integer from 1 to 4, n is an integer from 0 to 2, u is an integer from 0 to 1, $R^A$ is hydrogen, alkyl, arylalkyl, alkoxycarbonyl, or cycloalkyl, and $R^B$ is hydrogen or lower alkyl, or
b) $R^1$ is hydrogen or methyl and
   $R^2$ is —$[C(R^7)(R^8)]_u$-(Ring A), wherein $R^7$, $R^8$, and u are defined as above, and Ring A is of the formula:

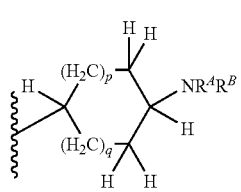

Ring A wherein $R^A$ and $R^B$ are as defined above, p is an integer from 0 to 2, and q is an integer from 0 to 2, or
c) $R^1$ is hydrogen or methyl, and
   $R^2$ is —$[C(R^7)(R^8)]_u$-(Ring B), wherein $R^7$, $R^8$, and u are defined as above, and Ring B is of the formula:

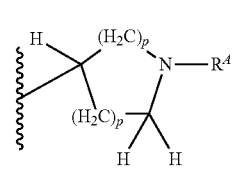

Ring B wherein $R^A$ is as defined above, p is an integer from 0 to 2, and q is an integer from 0 to 2, provided that p and u are not both equal to 0; or
d) $R^1$ and $R^2$ taken together with the nitrogen atom to which they are attached form Ring C of the formula:

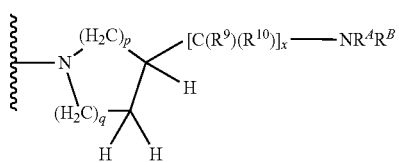

Ring C wherein $R^A$ and $R^B$ are defined as above, $R^9$ and $R^{10}$ are each independently hydrogen or lower alkyl; x is an integer from 0 to 2, p is an integer from 0 to 2, and q is an integer from 0 to 2, provided that p and x are not both equal to 0;

or e) $R^1$ and $R^2$ taken together with the nitrogen atom to which they are attached form Ring D of the formula:

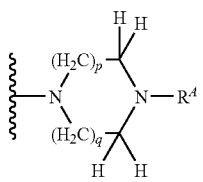

Ring D wherein $R^A$ is as defined above, p is an integer from 0 to 2, and q is an integer from 0 to 2, or f) $R^1$ and $R^2$ taken together with the nitrogen atom to which they are attached form Ring E of the formula:

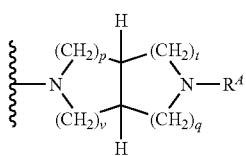

Ring E wherein $R^A$ is defined as above, p is an integer from 0 to 2, q is an integer from 0 to 2, v is an integer from 1 to 2, and t is an integer from 1 to 3, or g) $R^1$ and $R^2$ taken together with the nitrogen atom to which they are attached form Ring F of the formula:

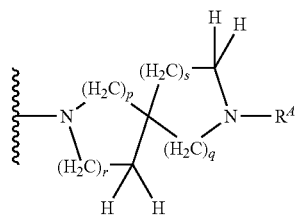

Ring F wherein $R^A$ is defined as above, r is an integer from 0 to 2, s is an integer from 0 to 2, p is an integer from 0 to 2, and q is an integer from 0 to 2, provided that p and q are not both equal to 0; and further provided that p is 1 or 2 when r is 0 and q is 1 or 2 when s is 0, with a pharmaceutically acceptable carrier.

The compositions comprise compounds of formula (I) or (Ia) formulated together with one or more non-toxic pharmaceutically acceptable carriers. The pharmaceutical compositions can be formulated for oral administration in solid or liquid form, for parenteral injection or for rectal administration.

One embodiment includes, but is not limited, compositions comprising a therapeutically effective amount of a compound of formula (I) or (Ia), as described for compounds of the invention, with a pharmaceutically acceptable carrier.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or non-aqueous solutions, dispersions, suspensions or emulsions and sterile powders for reconstitution into sterile injectable solutions or dispersions. Examples of suitable aqueous and non-aqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Opthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts or estersor amides derived from inorganic or organic acids. The term "pharmaceutically acceptable salts and esters and amides", as used herein, refer to carboxylate salts, amino acid addition salts, zwitterions, and esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. An example of a suitable salt is a hydrochloride salt.

Representative acid addition salts include, but are not limited to acetate, adipate, alginate, citrate, aspartate, benzoate, benzenesulfonate, bisulfate, butyrate, camphorate, camphorsulfonate, gluconate, glycerophosphate, hemisulfate, heptanoate, hexanoate, fumarate, hydrochloride, hydrobromide, hydroiodide, 2-hydroxyethansulfonate(isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid, tartaric acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylamine, dimethylamine, trimethylamine, triethylamine, diethylamine, ethylamine and the such as. Other representative organic amines useful for the formation of base addition salts include ethylenediamine, ethanolamine, diethanolamine, piperidine, and piperazine.

The invention contemplates pharmaceutically active compounds either chemically synthesized or formed by in vivo biotransformation to compounds of formula (I) or (Ia).

Methods of the Invention

The compounds and compositions of formula (I) or (Ia), as described for Compounds of the Invention and Compositions of the Invention, respectively, are useful for treating and preventing certain diseases and disorders in humans and animals. As an important consequence of the ability of these compounds to modulate the effects of histamine-3 receptors in cells, the compounds can affect physiological processes in humans and animals. In this way, the compounds and compositions described herein are useful for treating and preventing diseases and disorders modulated by histamine-3 receptors. Typically, treatment or prevention of such diseases and disorders can be effected by selectively modulating the histamine-3 receptors in a mammal, by administering a compound or composition of formula (Ia), either alone or in combination with another active agent as part of a therapeutic regimen.

The compounds of formula (Ia) and (I), including but not limited to those specified in the examples, possess an affinity for the histamine-3 receptors and therefore, the compounds of the invention may be useful for the treatment and prevention of diseases or conditions such as sleep disorders, migraines, pain, inflammation, cardiovascular dysfunction, and gastrointestinal dysfunction. The ability of histamine-3 receptor agonists, and consequently the compounds of formula (Ia), to prevent or treat such disorders is demonstrated by examples found in the following references.

The ability of histamine-3 receptor agonists, and thus the compounds of formula (Ia) or (I), including, but not limited to, those specified in the examples, to treat sleep disorders, may be demonstrated by Lin, J. S.; et al.; *Brain Research* 1990, 523(2), 325-330; Sakai, N.; et al.; *Life Sciences* 1991, 48(25), 2397-2404; Monti, J. M.; et al.; *European Journal of Pharmacology* 1991, 205(3), 283-287; Lin, J. S.; et al.; Monti, J. M.; et al.; *Life Sciences* 1993, 53, 1331-1338; *Journal of Neuroscience* 1996, 16(4), 1523-37; Monti, J. M.; et al.; *Neuropsychopharmacology* 1996 15(1), 31-35; Leurs, R.; et al.; *Trends in Pharmacological Sciences* 1998, 19(5), 177-183; McLeod, R. L.; et al.; *Journal of Pharmacology and Experimental Therapeutics* 1998, 287(1), 43-50; Brown, R. E.; et al.; *Progress in Neurobiology* 2001, 63(6), 637-672; Vanni-Mercier, G.; et al.; *Behavioural Brain Research* 2003, 144(1-2), 227-241; and Parmentier, R.; et al.; *Biochemical Pharmacology* 2007, 73(8), 1157-1171.

The ability of histamine-3 receptor agonists, and thus the compounds of formula (Ia) or (I), including, but not limited to, those specified in the examples, to treat migraines, may be demonstrated by Matsubara, T.; et al.; *European Journal of Pharmacology* 1992, 224, 145; Lassen, L. H.; et al.; *European Journal of Clinical Pharmacology* 1996, 49(5), 335-339; and McLeod, R. L.; et al.; *Journal of Pharmacology and Experimental Therapeutics* 1998, 287(1), 43-50.

The ability of histamine-3 receptor agonists, and thus the compounds of formula (Ia) or (I), including, but not limited to, those specified in the examples, to treat pain, may be demonstrated by Rouleau, A.; et al.; *Journal of Pharmacology and Experimental Therapeutics* 1997, 281, 1085-1094; Rouleau, A.; et al.; *Journal of Pharmacology and Experimental Therapeutics* 2000, 295, 219-225; Cannon, K. E.; et al.; *European Journal of Pharmacology* 2003, 470(3), 139-147; Cannon, K. E.; et al.; *Journal of Pain* 2005, 6(3), 193-200; and Cannon, K. E.; et al.; *Pharmacology, Biochemistry and Behavior* 2007, 88(1), 122-129.

The ability of histamine-3 receptor agonists, and thus the compounds of formula (Ia) or (I), including, but not limited to, those specified in the examples, to treat inflammatory disorders, may be demonstrated by Rouleau, A.; et al.; *Journal of Pharmacology and Experimental Therapeutics* 1997, 281, 1085-1094; Rouleau, A.; et al.; *Journal of Pharmacology and Experimental Therapeutics* 2000, 295, 219-225; and Cannon, K. E.; et al.; *Pharmacology, Biochemistry and Behavior* 2007, 88(1), 122-129.

The ability of histamine-3 receptor agonists, and thus the compounds of formula (Ia) or (I), including, but not limited to, those specified in the examples, to treat cardiovascular dysfunction may be demonstrated by Goethert, M.; et al.; *Canadian Journal of Physiology and Pharmacology* 1995, 73(5), 558-64; Malinowska, B.; et al.; *Journal of Physiology and Pharmacology* 1998, 49(2), 191-211; Levi, R.; et al.; *Journal of Pharmacology and Experimental Therapeutics* 2000, 292(3), 825-830; Mackins, C. J.; et al.; *Expert Opinion on Investigational Drugs* 2000, 9(11), 2537-2542; Silver, R. B.; et al.; *Proceedings of the National Academy of Sciences of the United States of America* 2001, 98(5), 2855-2859; WO2002/064212A1; Silver, R. B.; et al.; *Proceedings of the National Academy of Sciences of the United States of America* 2002, 99(1), 501-506; Koyama, M.; et al.; *Molecular Pharmacology* 2003, 63(2), 378-382; Koyama, M.; et al.; *Biochemical and Biophysical Research Communications* 2003, 306(3), 792-796; Seyedi, N.; et al.; *Journal of Pharmacology and Experimental Therapeutics* 2005, 312(1), 217-280; and Levi, R.; et al.; and *Biochemical Pharmacology* 2007, 73(8), 1146-1156.

The ability of the compounds of formula (Ia) or (I), including, but not limited to, those specified in the examples, to treat gastrointestinal dysfunction may be demonstrated by Prinz, C.; et al.; *Gastroenterology* 1993, 105, 449-461; Bertaccini, G. and Coruzzi, G.; *Digestive Diseases and Sciences* 1995, 40(9), 2052-2063; Morini, G.; et al.; *Digestion* 1995, 56, 145-152; Barocelli, E.; et al.; *British Journal of Pharmacology* 1995, 115, 1326-1330; and Soldani, G.; et al.; and *Journal of Gastroenterology* 1996, 31, 631-638.

The ability of the compounds of formula (Ia) or (I), including, but not limited to, those specified in the examples, to treat obesity may be demonstrated by Yoshimoto, R., et al.; *Proceedings of the National Academy of Sciences,* 2006, 103(37), 13866-13871.

The ability of the compounds of formula (Ia) or (I), including, but not limited to, those specified in the examples, to treat cholestatic liver disease may be demonstrated by Francis, H., et al.; *Laboratory Investigation,* 2007, 87, 473-487.

Compounds of formula (Ia) or (I) are particularly useful for treating sleep disorders.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of formula (Ia) or (I) can be employed in pure form or, where such forms exist, in pharmaceutically acceptable salt. Alternatively, the compound can be administered as a pharmaceutical composition containing the compound of interest in combination with one or more pharmaceutically acceptable carriers. The phrase "therapeutically effective amount" of the compound of formula (Ia) means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 30 mg/kg/day. For purposes of oral administration, more preferable doses can be in the range of from about 0.0003 to about 1 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples, which are intended as an illustration of and not a limitation upon the scope of the invention.

REFERENCE EXAMPLE

Reference Example 1

5-bromo-4,6-dichloropyrimidin-2-amine

Bromine (0.85 mL, 0.0166 mole) was added dropwise over 20 minutes to a stirred suspension of 2-amino-4,6-dichloropyrimidine (CAS#56-05-3, 1.70 g, 0.01037 mole) and sodium carbonate (1.00 g, 0.01244 mole) in 1:1 methanol/water (30 mL) at ambient temperature. Ten minutes after the addition was complete, more sodium carbonate (0.78 g, 0.0093 mole) was added to the reaction mixture. The reaction mixture was stirred at ambient temperature for 42 hours, then it was diluted with aqueous sodium bicarbonate to provide 5-bromo-4,6-dichloropyrimidin-2-amine as a precipitate that was collected by filtration and rinsed with water. The vacuum-dried solid weighed 2.11 g (83.7% yield). $^1$H NMR (300 MHz, d$_6$-DMSO) δ ppm 7.67 (s, 1H), 7.70 (s, 1H). MS (DCl—NH$_3$) m/z=241 (M+H)$^+$, m/z=258 (M+NH$_4$)$^+$.

EXAMPLES

Example 1

N$^4$-(2-aminoethyl)pyrimidine-2,4-diamine(2R,3R)-2,3-dihydroxysuccinate

Example 1A tert-butyl 2-(2-amino-5-bromo-6-chloropyrimidin-4-ylamino)ethylcarbamate A stirred solution of 5-bromo-4,6-dichloropyrimidin-2-amine (Reference Example 1, 14.00 g, 0.0576 mole), and triethylamine (41.8 mL, 0.2997 mole) in DMF (55 mL) was treated with tert-butyl 2-aminoethylcarbamate (9.24 g, 0.0576 mole). The reaction mixture was stirred at ambient temperature for 18 hours, then volatiles were removed under reduced pressure and the residue was partitioned between ethyl acetate and saturated aqueous sodium carbonate. The organic layer was dried (MgSO$_4$) and filtered. The filtrate was concentrated under reduced pressure to give a yellow solid that was triturated with ether to remove color. The ether-insoluble material was collected by filtration and dried under vacuum to provide tert-butyl 2-(2-amino-5-bromo-6-chloropyrimidin-4-ylamino)ethylcarbamate (18.02 g, 85.2% yield). $^1$H NMR (300 MHz, CD$_3$OD) δ ppm 1.42 (s, 9H), 3.25 (t, J=6 Hz, 2H), 3.47 (t, J=6 Hz, 2H). MS (DCl—NH$_3$) m/z=366 (M+H)$^+$.

Example 1B tert-butyl 2-(2-aminopyrimidin-4-ylamino)ethylcarbamate

A solution of tert-butyl 2-(2-amino-5-bromo-6-chloropyrimidin-4-ylamino)ethylcarbamate (Example 1A, 18.60 g, 0.0507 mole), triethylamine (135.0 mL, 0.9686 mole), and 10% palladium on charcoal (7.40 g) in 1:1 ethyl acetate/methanol (500 mL) was treated with hydrogen (60 psi) for two days. Insoluble material was removed by filtration through a pad of diatomaceous earth and the filtrate was concentrated under reduced pressure. The residue was partitioned between ethyl acetate and dilute aqueous sodium hydroxide. The organic layer was dried (MgSO$_4$) and filtered. The filtrate was concentrated under reduced pressure to give tert-butyl 2-(2-aminopyrimidin-4-ylamino)ethylcarbamate as a white, amorphous solid (12.7 g, 98.8% yield). $^1$H NMR (300 MHz, CD$_3$Cl$_3$) δ ppm 1.44 (s, 9H), 3.27-3.37 (m, 2H), 3.37-3.47 (m, 2H), 5.00 (s$_{br}$, 2H), 5.28 (s$_{br}$, 1H), 5.52 (s$_{br}$, 1H), 5.78 (d, J=6 Hz, 1H), 7.76 (d, J=6 Hz, 1H). MS (DCl—NH$_3$) m/z=254 (M+H)$^+$.

Example 1C

N$^4$-(2-aminoethyl)pyrimidine-2,4-diamine(2R,3R)-2,3-dihydroxysuccinate

A stirred solution of tert-butyl 2-(2-aminopyrimidin-4-ylamino)ethylcarbamate (Example 1B, 12.70 g, 0.0501 mole) in dichloromethane (200 mL) was treated with trifluoroacetic acid (175 mL, 2.2714 mole). After stirring at ambient temperature for four hours, volatiles were removed under reduced pressure to give a yellow oil. This oil was dissolved in methanol. This solution was chilled to 0° C. and treated with excess solid potassium hydroxide. The mixture was stirred overnight while warming to ambient temperature. Volatiles were removed under reduced pressure and the residue was stirred with chloroform. Insoluble material was removed by filtration. The filtrate was dried (MgSO$_4$) and filtered. The filtrate was concentrated under reduced pressure to give a white solid that was purified by column chromatography on silica gel, eluting with 90:9:1 to 75:23:2 CHCl$_3$/MeOH/Et$_3$N. Fractions containing product were combined and concentrated under reduced pressure. The residue was dissolved in hot CHCl$_3$ and the solution was dried (MgSO$_4$) and filtered. The filtrate was concentrated under reduced pressure to give a solid that was dried under high vacuum. The solid was dissolved in methanol and this solution was treated with a methanol solution of L-tartaric acid. After stirring at ambient temperature for one hour, crystals were collected by filtration then dried overnight under high vacuum to provide N$^4$-(2-aminoethyl)pyrimidine-2,4-diamine(2R,3R)-2,3-dihydroxysuccinate (3.445 g, 22.7% yield). $^1$H NMR (300 MHz, D$_2$O) δ ppm 3.28 (t, J=6 Hz, 2H), 3.79 (t, J=6 Hz, 2H), 4.33 (s, 2H), 6.19 (d, J=7 Hz, 1H), 7.60 (d, J=6 Hz, 1H). MS (ESI) m/z=154 (M+H)$^+$.

Example 2

N$^4$-(2-(dimethylamino)ethyl)pyrimidine-2,4-diamine 2,2,2-trifluoroacetate $^1$H NMR (300 MHz, d$_6$-DMSO) δ ppm 2.85 (s, 6H), 3.29 (t, J=6 Hz, 2H), 3.69 (q, J=6 Hz, 2H), 6.10 (d, J=7 Hz, 1H), 7.72 (d, J=7 Hz, 1H), 7.97 (s$_{br}$, 2H), 8.94 (t, J=6 Hz, 1H), 9.68 (s$_{br}$, 1H). MS (DCl—NH$_3$) m/z=182 (M+H)$^+$.

Example 3

N$^4$-(2-(dimethylamino)ethyl)-N$^4$-methylpyrimidine-2,4-diamine dihydrochloride A mixture of 4-chloropyrimidin-2-amine (CAS#3993-78-0, 0.100 g, 0.00077 mole), N$^1$,N$^1$,N$^2$-trimethylethane-1,2-diamine (CAS#142-25-6, 0.082 g, 0.00077 mole), and N-ethyl-N-isopropylpropan-2-amine (0.94 mL, 0.00540 mole) in n-propanol (2 mL) was heated at 200° C. under microwave irradiation for 15 minutes. Volatiles were removed under reduced pressure and the residue was partitioned between ethyl acetate and saturated aqueous sodium carbonate. The organic layer was dried (MgSO$_4$) and filtered. The filtrate was concentrated under reduced pressure and the residue was purified by chromatography with silica gel, eluting with 97:3:0.5 to 95:5:1 DCM/MeOH/Et$_3$N. Fractions containing product were combined and concentrated under reduced pressure. The residue was dissolved in ethyl acetate. This solution was dried (MgSO$_4$) and filtered. The filtrate was concentrated under reduced pressure and the residue was dissolved in a minimum of methanol. This solution was acidified with a 4.0 M solution of HCl in dioxane. Ether was added to induce crystallization. Crystals were collected by filtration to provide N$^4$-(2-(dimethylamino)ethyl)-N$^4$-methylpyrimidine-2,4-diamine dihydrochloride (0.035 g, 15.8% yield). $^1$H NMR (300 MHz, CD$_3$OD) δ ppm 3.00 (s, 6H), 3.25 (s, 3H), 3.46 (t, J=6 Hz, 2H), 4.14 (t, J=6 Hz, 2H), 6.40 (d, J=7 Hz, 1H), 7.75 (d, J=7 Hz, 1H). MS (DCl—NH$_3$) m/z=196 (M+H)$^+$.

Example 4

N$^4$-(2-aminopropyl)pyrimidine-2,4-diamine bis(2,2,2-trifluoroacetate) and N$^4$-(1-aminopropan-2-yl)pyrimidine-2,4-diamine bis(2,2,2-trifluoroacetate)

An inseparable mixture of the two title compounds was prepared by the method of Example 3, substituting five equivalents of propane-1,2-diamine in place of both $N^1,N^1,N^2$-trimethylethane-1,2-diamine and N-ethyl-N-isopropylpropan-2-amine and substituting n-butanol for n-propanol. The mixture of the final products was obtained following purification by silica gel chromatography eluting with 10-20% methanol in acetonitrile with 2% concentrated aqueous ammonium hydroxide. The mixture of products was dissolved in methanol and treated with excess trifluoroacetic acid. The volatiles were removed in vacuo to give the titled compounds as a trifluoroacetic acid salt. $^1$H NMR (300 MHz, CD$_3$OD) δ ppm $N^4$-(2-aminopropyl)pyrimidine-2,4-diamine bis(2,2,2-trifluoroacetate): 1.35 (d, J=7 Hz, 3H), 3.44-3.52 (m, 1H), 4.02 (t, J=11 Hz, 1H), 4.28-4.43 (m, 1H), 6.16 (d, J=7 Hz, 1H), 7.64 (d, J=7 Hz, 1H). $N^4$-(1-aminopropan-2-yl)pyrimidine-2,4-diamine bis(2,2,2-trifluoroacetate): 1.33 (d, J=7 Hz, 3H), 3.21-3.28 (m, 1H), 3.80 (t, J=9 Hz, 1H), 4.07-4.18 (m, 1H), 6.12 (d, J=7 Hz, 1H), 7.62 (d, J=7 Hz, 1H). MS (ESI) m/z=168 (M+H)$^+$.

Example 5

$N^4$-(2-amino-2-methylpropyl)pyrimidine-2,4-diamine bis(2,2,2-trifluoroacetate) and $N^4$-(1-amino-2-methylpropan-2-yl)pyrimidine-2,4-diamine bis(2,2,2-trifluoroacetate)

An inseparable mixture of the two title compounds was prepared by the method of Example 3, substituting five equivalents of 2-methylpropane-1,2-diamine in place of both $N^1,N^1,N^2$-trimethylethane-1,2-diamine and N-ethyl-N-isopropylpropan-2-amine and substituting n-butanol for n-propanol. The mixture of the final products was obtained following purification by silica gel chromatography eluting with 10-20% methanol in acetonitrile with 2% concentrated aqueous ammonium hydroxide. The mixture of products was dissolved in methanol and treated with excess trifluoroacetic acid. The volatiles were removed in vacuo to give the titled compounds as a trifluoroacetic acid salt. $^1$H NMR (300 MHz, CD$_3$OD) δ ppm $N^4$-(2-amino-2-methylpropyl)pyrimidine-2,4-diamine bis(2,2,2-trifluoroacetate): 1.40 (s, 6H), 3.67 (s, 2H), 6.19 (d, J=7 Hz, 1H), 7.66 (d, J=7 Hz, 1H). $N^4$-(1-amino-2-methylpropan-2-yl)pyrimidine-2,4-diamine bis(2,2,2-trifluoroacetate): 1.42 (s, 6H), 3.66 (s, 2H), 6.19 (d, J=7 Hz, 1H), 7.66 (d, J=7 Hz, 1H). MS (ESI) m/z=182 (M+H)$^+$.

Example 6

$N^4$-(3-aminopropyl)pyrimidine-2,4-diamine dihydrochloride

The title compound was prepared by a sequence of reactions similar to that used in the preparation of Example 1. Thus, the method of Example 1A, was repeated, substituting tert-butyl 3-aminopropylcarbamate in place of tert-butyl 2-aminoethylcarbamate to provide the intermediate, tert-butyl 3-(2-amino-5-bromo-6-chloropyrimidin-4-ylamino)propylcarbamate. This intermediate was dehalogenated by the method of Example 1B to provide tert-butyl 3-(2-aminopyrimidin-4-ylamino)propylcarbamate. A methanol solution of this dehalogenated product was then treated with 17.8 equivalents of 4M HCl in dioxane at ambient temperature for 18 hours. Volatiles were removed under reduced pressure and the residue was crystallized from methanol/ether to provide white crystals of $N^4$-(3-aminopropyl)pyrimidine-2,4-diamine dihydrochloride. $^1$H NMR (300 MHz, D$_2$O) δ ppm 1.87 (q, J=7 Hz, 2H), 2.95 (t, J=7 Hz, 2H), 3.41 (t, J=7 Hz, 2H), 5.99 (d, J=7 Hz, 1H), 7.47 (d, J=6 Hz, 1H). MS (DCl—NH$_3$) m/z=168 (M+H)$^+$.

Example 7

$N^4$-(3-(methylamino)propyl)pyrimidine-2,4-diamine dihydrochloride

Example 7A tert-butyl 3-(2-aminopyrimidin-4-ylamino)propyl(methyl)carbamate

A solution of 4-chloropyrimidin-2-amine (CAS#3993-78-0, 0.200 g, 0.0015 mole), N-ethyl-N-isopropylpropan-2-amine (1.88 mL, 0.0108 mole), and tert-butyl 3-aminopropyl(methyl)carbamate (0.300 g, 0.0015 mole) in n-propanol (3 mL) was heated at 200° C. under microwave irradiation for 10 minutes. Volatiles were removed under reduced pressure and the residue was partitioned between ethyl acetate and saturated aqueous sodium carbonate. The organic layer was dried (MgSO$_4$) and filtered. The filtrate was concentrated under reduced pressure and the residue was purified by column chromatography on silica gel eluting with 97:3:trace DCM/MeOH/aq. NH$_4$OH. Two major products were isolated. The first product to elute was the isomeric byproduct, tert-butyl 3-((2-aminopyrimidin-4-yl)(methyl)amino)propylcarbamate. The second product to elute was the desired product, tert-butyl 3-(2-aminopyrimidin-4-ylamino)propyl(methyl)carbamate (0.040 g, 9.2%). $^1$H NMR (300 MHz, CD$_3$OD) δ ppm 1.43 (s, 9H), 1.79 (pentet, J=7 Hz, 2H), 2.86 (s, 3H), 3.26-3.33 (m, 4H), 5.81 (d, J=6 Hz, 1H), 7.58 (d, J=6 Hz, 1H). MS (DCl—NH$_3$) m/z=282 (M+H)$^+$.

Example 7B $N^4$-(3-(methylamino)propyl)pyrimidine-2,4-diamine dihydrochloride A stirred solution of tert-butyl 3-(2-aminopyrimidin-4-ylamino)propyl(methyl)carbamate (Example 7A, 40 mg, 0.1422 mmol) in methanol (0.5 mL) was treated with a 4M solution of HCl in dioxane (0.5 mL, 2.0000 mmol). After stirring at ambient temperature for 18 hours, volatiles were removed under reduced pressure to give a white solid that was crystallized methanol/ether. White crystals were collected by filtration to provide $N^4$-(3-(methylamino)propyl)pyrimidine-2,4-diamine dihydrochloride (6.0 mg, 16.6% yield). $^1$H NMR (300 MHz, CD$_3$OD) δ ppm 2.01 (pentet, J=7 Hz, 2H), 2.72 (s, 3H), 3.07 (t, J=7 Hz, 2H), 3.58 (t, J=7 Hz, 2H), 6.13 (d, J=7 Hz, 1H), 7.58 (d, J=7 Hz, 1H). MS (DCl—NH$_3$) m/z=182 (M+H)$^+$.

Example 8

$N^4$-(3-aminopropyl)-$N^4$-methylpyrimidine-2,4-diamine dihydrochloride

The early eluting, isomeric byproduct, tert-butyl 3-((2-aminopyrimidin-4-yl)(methyl)amino)propylcarbamate from Example 7A was treated with a 4M solution of HCl in dioxane by the method of Example 7B to provide $N^4$-(3-aminopropyl)-$N^4$-methylpyrimidine-2,4-diamine dihydrochloride (8.4 mg, 31.3% yield). $^1$H NMR (300 MHz, CD$_3$OD) δ ppm 2.03 (pentet, J=7 Hz, 2H), 2.97 (t, J=7 Hz, 2H), 3.21 (s, 3H), 3.84

(t, J=7 Hz, 2H), 6.39 (d, J=8 Hz, 1H), 7.73 (d, J=8 Hz, 1H). MS (DCl—NH$_3$) m/z=182 (M+H)$^+$.

Example 9

N$^4$-(3-(dimethylamino)propyl)-N$^4$-methylpyrimidine-2,4-diamine(2R,3R)-2,3-dihydroxysuccinate The title compound was prepared by the method of Example 7A, substituting N$^1$,N$^1$,N$^3$-trimethylpropane-1,3-diamine in place of tert-butyl 3-aminopropyl(methyl)carbamate to provide the free base of the title compound. A solution of this free base in methanol was treated with a solution of one equivalent of L-tartaric acid in methanol to provide N$^4$-(3-(dimethylamino)propyl)-N$^4$-methylpyrimidine-2,4-diamine(2R,3R)-2,3-dihydroxysuccinate. $^1$H NMR (300 MHz, CD$_3$OD) δ ppm 2.06 (pentet, J=7 Hz, 2H), 2.82 (s, 6H), 3.05 (t, J=7 Hz, 2H), 3.15 (s, 3H), 3.71 (t, J=7 Hz, 2H), 4.38 (s, 2H), 6.28 (d, J=7 Hz, 1H), 7.73 (d, J=7 Hz, 1H). MS (DCl—NH$_3$) m/z=210 (M+H)$^+$.

Example 10

N$^4$-(3-aminopentyl)pyrimidine-2,4-diamine and N$^4$-(1-aminopentan-3-yl)pyrimidine-2,4-diamine An inseparable mixture of the two title compounds was prepared by the method of Example 3, substituting five equivalents of pentane-1,3-diamine in place of both N$^1$,N$^1$,N$^2$-trimethylethane-1,2-diamine and N-ethyl-N-isopropylpropan-2-amine and substituting n-butanol for n-propanol. The mixture of the crude products was obtained following silica gel chromatography eluting with 10-20% methanol in acetonitrile with 2% concentrated aqueous ammonium hydroxide. The mixture of products was dissolved in methanol and treated with excess trifluoroacetic acid. The volatiles were removed in vacuo to give the titled compounds as a trifluoroacetic acid salt. A final purification of the compound was achieved by reverse-phase HPLC (column, Waters Xterra® C18; eluent, aqueous ammonium bicarbonate/acetonitrile) giving the title compounds. $^1$H NMR (300 MHz, CD$_3$OD) δ ppm 0.97-1.07 (m, 3H), 1.53-2.07 (m, 4H), 3.16 (pentet, J=6 Hz, 1H), 3.49-3.69 (m, 2H), 6.10 (d, J=7 Hz, 1H), 7.58 (d, J=7 Hz, 1H). MS (ESI) m/z=196 (M+H)$^+$.

Example 11

N$^4$-(3-amino-2,2-dimethylpropyl)pyrimidine-2,4-diamine

The title compound was prepared by the method of Example 3, substituting five equivalents of 2,2-dimethylpropane-1,3-diamine in place of both N$^1$,N$^1$,N$^2$-trimethylethane-1,2-diamine and N-ethyl-N-isopropylpropan-2-amine and substituting n-butanol for n-propanol. The crude product was obtained following silica gel chromatography eluting with 10-20% methanol in acetonitrile with 2% concentrated aqueous ammonium hydroxide. The product was dissolved in methanol and treated with excess trifluoroacetic acid. The volatiles were removed in vacuo to give the titled compound as a trifluoroacetic acid salt. A final purification of the compound was achieved by reverse-phase HPLC (column, Waters Xterra® C18; eluent, aqueous ammonium bicarbonate/acetonitrile) giving the title compound. $^1$H NMR (300 MHz, CD$_3$OD) δ ppm 0.91 (s, 3H), 2.35 (s, 2H), 3.23 (s, 2H), 5.83 (d, J=6 Hz, 1H), 7.55 (d, J=6 Hz, 1H). MS (ESI) m/z=196 (M+H)$^+$.

Example 12

N$^4$-(1-benzylpiperidin-4-yl)pyrimidine-2,4-diamine 2,2,2-trifluoroacetate $^1$H NMR (300 MHz, d$_6$-DMSO) δ ppm 1.66-1.83 (m, 2H), 1.95-2.21 (m, 3H), 2.90-3.03 (m, 2H), 3.36-3.49 (m, 1H), 3.94-4.04 (m, 1H), 4.31 (s, 2H), 6.05 (d, J=7 Hz, 1H), 7.45-7.69 (m, 5H), 7.78 (s$_{br}$, 1H), 8.81 (d, J=7 Hz, 1H), 9.96 (s$_{br}$, 1H), 11.87 (s$_{br}$, 2H). MS (ESI) m/z=284 (M+H)$^+$.

Example 13

4-(4-methylpiperazin-1-yl)pyrimidin-2-amine

The title compound was prepared in two steps, first by the method of Example 1A, substituting 1-methylpiperazine in place of tert-butyl 2-aminoethylcarbamate to give the intermediate, 5-bromo-4-chloro-6-(4-methylpiperazin-1-yl)pyrimidin-2-amine. This intermediate was then dehalogenated by the method of Example 1B to provide 4-(4-methylpiperazin-1-yl)pyrimidin-2-amine. $^1$H NMR (300 MHz, CD$_3$OD) δ ppm 2.32 (s, 3H), 2.48 (t, J=5 Hz, 4H), 3.65 (t, J=5 Hz, 4H), 6.09 (d, J=6 Hz, 1H), 7.73 (d, J=6 Hz, 1H). MS (DCl—NH$_3$) m/z=194 (M+H)$^+$.

Example 14 tert-butyl 4-(2-aminopyrimidin-4-yl)piperazine-1-carboxylate

Example 14A tert-butyl 4-(2-amino-6-chloropyrimidin-4-yl)piperazine-1-carboxylate A mixture of 4,6-dichloropyrimidin-2-amine (1.500 g, 0.0091 mole), tert-butyl piperazine-1-carboxylate (2.044 g, 0.0110 mole), and N-ethyl-N-isopropylpropan-2-amine (11.1 mL, 0.0637 mole) in ethanol (20 mL) was magnetically stirred in a sealed tube at 80° C. for 18 hours. After cooling to ambient temperature, the seal was broken and volatiles were removed under reduced pressure. The residue was partitioned between ethyl acetate and saturated aqueous sodium carbonate. The organic layer was dried (MgSO$_4$) and filtered. The filtrate was concentrated under reduced pressure to give a crude, white solid that was crystallized from hot methanol. The crystals were collected by filtration and dried under vacuum to provide tert-butyl 4-(2-amino-6-chloropyrimidin-4-yl)piperazine-1-carboxylate (1.95 g, 68.3% yield). $^1$H NMR (300 MHz, CDCl$_3$) δ ppm 1.48 (s, 9H), 3.46-3.52 (m, 4H), 3.55-3.61 (m, 4H), 4.90 (s$_{br}$, 2H), 5.96 (s, 1H). MS (DCl—NH$_3$) m/z=314 (M+H)$^+$.

Example 14B tert-butyl 4-(2-aminopyrimidin-4-yl)piperazine-1-carboxylate

The title compound was prepared by the method of Example 1B, substituting tert-butyl 4-(2-amino-6-chloropyrimidin-4-yl)piperazine-1-carboxylate (Example 14A) in place of tert-butyl 2-(2-amino-5-bromo-6-chloropyrimidin-4-ylamino)ethylcarbamate. The free base was purified by crystallization from ethanol/ether to provide, after drying under vacuum, tert-butyl 4-(2-aminopyrimidin-4-yl)piperazine-1-carboxylate (0.861 g, 49.6% yield). $^1$H NMR (300

MHz, d₆-DMSO) δ ppm 1.42 (s, 9H), 3.30-3.38 (m, 4H), 3.47-3.53 (m, 4H), 6.01 (d, J=6 Hz, 1H), 7.77 (d, J=6 Hz, 1H). MS (DCl—NH₃) m/z=280 (M+H)⁺.

Example 15 tert-butyl 4-((2-aminopyrimidin-4-ylamino)methyl) piperidine-1-carboxylate

The title compound was prepared in two steps, first by the method of Example 14A, substituting tert-butyl 4-(aminomethyl)piperidine-1-carboxylate in place of tert-butyl piperazine-1-carboxylate to give the intermediate, tert-butyl 4-((2-amino-6-chloropyrimidin-4-ylamino)methyl)piperidine-1-carboxylate. This intermediate was then dehalogenated by the method of Example 1B to provide tert-butyl 4-((2-aminopyrimidin-4-ylamino)methyl)piperidine-1-carboxylate. ¹H NMR (300 MHz, CD₃OD) δ ppm 1.03-1.19 (m, 2H), 1.45 (s, 9H), 1.68-1.86 (m, 3H), 2.67-2.82 (m, 2H), 3.17-3.23 (m, 2H), 4.04-4.11 (m, 2H), 7.82 (d, J=6 Hz, 1H), 7.57 (d, J=6 Hz, 1H). MS (DCl—NH₃) m/z=308 (M+H)⁺.

Example 16

Trans-N⁴-(4-aminocyclohexyl)pyrimidine-2,4-diamine

¹H NMR (400 MHz, d₆-DMSO) δ ppm 1.41-1.71 (m, 8H), 2.72-2.88 (m, 1H), 3.72-3.96 (m, 1H), 5.76 (s_br, 3H), 6.52-6.75 (m, 1H), 7.49-7.60 (m, 1H). MS (DCl—NH₃) m/z=208 (M+H)⁺.

Example 17

(R)-tert-butyl 3-(2-aminopyrimidin-4-ylamino)pyrrolidine-1-carboxylate

The title compound was prepared in two steps, first by the method of Example 14A, substituting (R)-tert-butyl 3-aminopyrrolidine-1-carboxylate in place of tert-butyl piperazine-1-carboxylate to give the intermediate, (R)-tert-butyl 3-(2-amino-6-chloropyrimidin-4-ylamino)pyrrolidine-1-carboxylate. This intermediate was then dehalogenated by the method of Example 1B to provide (R)-tert-butyl 3-(2-aminopyrimidin-4-ylamino)pyrrolidine-1-carboxylate. ¹H NMR (300 MHz, CD₃OD) δ ppm 1.45 (s, 9H), 1.82-1.97 (m, 1H), 2.00-2.25 (m, 1H), 3.16-3.23 (m, 1H), 3.34-3.54 (m, 2H), 3.60-3.68 (m, 1H), 4.39-4.52 (m, 1H), 5.83 (d, J=6 Hz, 1H), 7.60 (d, J=6 Hz, 1H). MS (DCl—NH₃) m/z=280 (M+H)⁺.

Example 18

(R)—N⁴-(pyrrolidin-3-yl)pyrimidine-2,4-diamine dihydrochloride

The title compound was prepared by the method of Example 7B, substituting (R)-tert-butyl 3-(2-aminopyrimidin-4-ylamino)pyrrolidine-1-carboxylate (Example 17) in place of tert-butyl 3-(2-aminopyrimidin-4-ylamino)propyl (methyl)carbamate to provide (R)—N⁴-(pyrrolidin-3-yl)pyrimidine-2,4-diamine dihydrochloride. ¹H NMR (300 MHz, CD₃OD) δ ppm 2.09-2.24 (m, 1H), 2.36-2.52 (m, 1H), 3.31-3.59 (m, 3H), 3.61-3.70 (m, 1H), 4.65-4.75 (m, 1H), 6.18 (d, J=7 Hz, 1H), 7.64 (d, J=7 Hz, 1H). MS (DCl—NH₃) m/z=180 (M+H)⁺.

Example 19

4-((3aR,6aS)-5-benzylhexahydropyrrolo[3,4-c]pyrrol-2(1H)-yl)pyrimidin-2-amine

The title compound was prepared by the method of Example 3, substituting (3aR,6aS)-2-benzyloctahydropyrrolo[3,4-c]pyrrole in place of N¹,N¹,N²-trimethylethane-1,2-diamine. ¹H NMR (300 MHz, CD₃OD) δ ppm 2.41-2.47 (m, 2H), 2.76-2.83 (m, 2H), 2.89-3.03 (m, 2H), 3.37-3.46 (m, 2H), 3.55-3.63 (m, 1H), 3.60 (s, 3H), 5.86 (d, J=6 Hz, 1H), 7.19-7.34 (m, 5H), 7.70 (d, J=6 Hz, 1H). MS (DCl—NH₃) m/z=296 (M+H)⁺.

Example 20

4-(4-aminopiperidin-1-yl)pyrimidin-2-amine dihydrochloride

The title compound was prepared in two steps, first by the method of Example 3, substituting tert-butyl piperidin-4-ylcarbamate in place of N¹,N¹,N²-trimethylethane-1,2-diamine to give the intermediate, tert-butyl 1-(2-aminopyrimidin-4-yl)piperidin-4-ylcarbamate. The Boc protecting group of this intermediate was then removed by the method of Example 7B to provide 4-(4-aminopiperidin-1-yl)pyrimidin-2-amine dihydrochloride. ¹H NMR (300 MHz, CD₃OD) δ ppm 1.52-1.68 (m, 2H), 2.11-2.22 (m, 2H), 3.02-3.30 (m, 1H), 3.44-3.58 (m, 1H), 4.05-4.75 (m, 1H), 4.80-5.35 (m, 1H), 6.54 (d, J=8 Hz, 1H), 7.72 (m, 1H). MS (DCl—NH₃) m/z=194 (M+H)⁺.

Example 21

4-(5-benzyl-1,5-diazocan-1-yl)pyrimidin-2-amine

The title compound was prepared by the method of Example 3, substituting 1-benzyl-1,5-diazocane in place of N¹,N¹,N²-trimethylethane-1,2-diamine. ¹H NMR (300 MHz, CD₃OD) δ ppm 1.62-1.82 (m, 4H), 2.60 (t, J=6 Hz, 4H), 3.51-3.66 (m, 2H), 3.63 (s, 2H), 3.69-3.82 (m, 2H), 5.91 (d, J=6 Hz, 1H), 7.15-7.33 (m, 5H), 7.67 (d, J=6 Hz, 1H). MS (DCl—NH₃) m/z=298 (M+H)⁺.

Example 22

N⁴-(azetidin-3-yl)pyrimidine-2,4-diamine trihydrochloride

The title compound was prepared in three steps, first by the method of Example 14A, substituting tert-butyl 3-aminoazetidine-1-carboxylate in place of tert-butyl piperazine-1-carboxylate to give the intermediate, tert-butyl 3-(2-amino-6-chloropyrimidin-4-ylamino)azetidine-1-carboxylate. This intermediate was then dehalogenated by the method of Example 1B to provide tert-butyl 3-(2-aminopyrimidin-4-ylamino)azetidine-1-carboxylate. Finally, the Boc protecting group was removed from this dehalogenated intermediate by the method of Example 7B to provide N⁴-(azetidin-3-yl)pyrimidine-2,4-diamine trihydrochloride. ¹H NMR (300 MHz, D₂O) δ ppm 3.08-3.22 (m, 2H), 3.25-3.36 (m, 2H), 3.71-3.82 (m, 1H), 5.04 (d, J=7 Hz, 1H), 6.46 (d, J=6 Hz, 1H). MS (ESI) m/z=166 (M+H)⁺.

Example 23

4-(2,7-diazaspiro[3.5]nonan-7-yl)pyrimidin-2-amine trihydrochloride

The title compound was prepared in two steps, first by the method of Example 3, substituting tert-butyl 2,7-diazaspiro[3.5]nonane-2-carboxylate in place of $N^1,N^1,N^2$-trimethylethane-1,2-diamine to give the intermediate, tert-butyl 7-(2-aminopyrimidin-4-yl)-2,7-diazaspiro[3.5]nonane-2-carboxylate. The Boc protecting group of this intermediate was then removed by the method of Example 7B to provide 4-(2,7-diazaspiro[3.5]nonan-7-yl)pyrimidin-2-amine trihydrochloride. $^1$H NMR (300 MHz, D$_2$O) δ ppm 1.81-1.94 (m, 4H), 3.47-3.61 (m, 3H), 3.63-3.68 (m, 2H), 3.72-3.84 (m, 3H), 6.33 (d, J=7 Hz, 1H), 7.53 (d, J=7 Hz, 1H). MS (ESI) m/z=220 (M+H)$^+$.

Example 24

N$^4$-(piperidin-4-yl)pyrimidine-2,4-diamine dihydrochloride

The title compound was prepared in two steps, first by the method of Example 3, substituting tert-butyl 4-aminopiperidine-1-carboxylate in place of $N^1,N^1,N^2$-trimethylethane-1,2-diamine to give the intermediate, tert-butyl 4-(2-aminopyrimidin-4-ylamino)piperidine-1-carboxylate. The Boc protecting group of this intermediate was then removed by the method of Example 7B to provide N$^4$-(piperidin-4-yl)pyrimidine-2,4-diamine dihydrochloride. $^1$H NMR (300 MHz, D$_2$O) δ ppm 1.59-1.75 (m, 2H), 2.08-2.19 (m, 2H), 2.99-3.11 (m, 2H), 3.33-3.43 (m, 2H), 4.11-4.22 (m, 1H), 5.98 (d, J=7 Hz, 1H), 7.41 (d, J=7 Hz, 1H). MS (DCl—NH$_3$) m/z=194 (M+H)$^+$.

Example 25

4-(piperazin-1-yl)pyrimidin-2-amine dihydrochloride

The title compound was prepared by the method of Example 7B, substituting tert-butyl 4-(2-aminopyrimidin-4-yl)piperazine-1-carboxylate (Example 14B) in place of tert-butyl 3-(2-aminopyrimidin-4-ylamino)propyl(methyl)carbamate (Example 7A). $^1$H NMR (300 MHz, D$_2$O) δ ppm 3.27-3.33 (m, 4H), 3.86-4.12 (m, 4H), 6.37 (d, J=8 Hz, 1H), 7.64 (d, J=8 Hz, 1H). MS (DCl—NH$_3$) m/z=180 (M+H)$^+$.

In a manner similar to the methods described above additional compounds of the invention may be prepared as summarized in Table 2.

TABLE 2

Examples 26-51.

| Example Number | Starting diamines (HNR$^1$R$^2$) and CAS# | Product Structures | May be Prepared by the Method of (substituting the indicated starting diamine) |
| --- | --- | --- | --- |
| 26 | (S)-propane-1,2-diamine dihydrochloride CAS# 19777-66-3 | | Example 3, 5 equivalents of diamine |
| 27 | (R)-propane-1,2-diamine dihydrochloride CAS# 19777-67-4 | | Example 3, 5 equivalents of diamine |
| 28 | (S)-tert-butyl 3-aminopyrrolidine-1-carboxylate CAS # 147081-49-0 | | Example 7A followed by Example 7B |

TABLE 2-continued

Examples 26-51.

| Example Number | Starting diamines (HNR¹R²) and CAS# | Product Structures | May be Prepared by the Method of (substituting the indicated starting diamine) |
|---|---|---|---|
| 29 | (S)-tert-butyl pyrrolidin-3-ylcarbamate CAS # 122536-76-9 | 2-amino-4-[(S)-3-aminopyrrolidin-1-yl]pyrimidine | Example 7A followed by Example 7B |
| 30 | (R)-tert-butyl pyrrolidin-3-ylcarbamate CAS # 122536-77-0 | 2-amino-4-[(R)-3-aminopyrrolidin-1-yl]pyrimidine | Example 7A followed by Example 7B |
| 31 | tert-butyl azetidin-3-ylcarbamate CAS # 91188-13-5 | 2-amino-4-(3-aminoazetidin-1-yl)pyrimidine | Example 7A followed by Example 7B |
| 32 | tert-butyl 2,7-diazaspiro[3.5]nonane-7-carboxylate CAS # 236406-55-6 | 2-amino-4-(2,7-diazaspiro[3.5]nonan-2-yl)pyrimidine | Example 7A followed by Example 7B |
| 33 | tert-butyl 1,4-diazepane-1-carboxylate CAS # 112275-50-0 | 2-amino-4-(1,4-diazepan-1-yl)pyrimidine | Example 7A followed by Example 7B |
| 34 | tert-butyl 3,9-diazaspiro[5.5]undecane-3-carboxylate 173405-78-2 | 2-amino-4-(3,9-diazaspiro[5.5]undecan-3-yl)pyrimidine | Example 7A followed by Example 7B |

TABLE 2-continued

Examples 26-51.

| Example Number | Starting diamines (HNR¹R²) and CAS# | Product Structures | May be Prepared by the Method of (substituting the indicated starting diamine) |
|---|---|---|---|
| 35 | tert-butyl (1r,3r)-3-aminocyclobutyl-carbamate CAS # 871014-19-6 | | Example 7A followed by Example 7B |
| 36 | tert-butyl (1s,3s)-3-aminocyclobutyl-carbamate | | Example 7A followed by Example 7B |
| 37 | (1S,5S)-benzyl 3,6-diazabicyclo[3.2.0]heptane-3-carboxylate CAS # 370881-43-9 | | Example 7A followed by Example 1B |
| 38 | (1S,5R)-benzyl 3,6-diazabicyclo[3.2.0]heptane-3-carboxylate CAS # 370881-68-8 | | Example 7A followed by Example 1B |
| 39 | (1R,5S)-benzyl 3,6-diazabicyclo[3.2.0]heptane-3-carboxylate CAS # 799279-81-5 | | Example 7A followed by Example 7B |
| 40 | (1S,5R)-benzyl 3,6-diazabicyclo[3.2.0]heptane-6-carboxylate CAS # 370882-66-9 | | Example 7A followed by Example 7B |

TABLE 2-continued

Examples 26-51.

| Example Number | Starting diamines (HNR¹R²) and CAS# | Product Structures | May be Prepared by the Method of (substituting the indicated starting diamine) |
|---|---|---|---|
| 41 | (3aR,7aR)-2-benzyloctahydro-1H-pyrrolo[3,4-c]pyridine CAS # 870237-33-5 | | Example 7A followed by Example 1B |
| 42 | (3aS,7aR)-5-benzyloctahydro-1H-pyrrolo[3,4-c]pyridine CAS # 236406-57-8 | | Example 7A followed by Example 1B |
| 43 | (3aS,7aS)-5-benzyloctahydro-1H-pyrrolo[3,4-c]pyridine CAS # 159991-07-8 | | Example 7A followed by Example 1B |
| 44 | (4aS,7aS)-tert-butyl octahydro-1H-pyrrolo[3,4-b]pyridine-1-carboxylate CAS # 159991-07-8 | | Example 7A followed by Example 7B |
| 45 | (4aR,7aR)-tert-butyl octahydro-1H-pyrrolo[3,4-b]pyridine-1-carboxylate CAS # 186201-89-8 | | Example 7A followed by Example 7B |

TABLE 2-continued

Examples 26-51.

| Example Number | Starting diamines (HNR¹R²) and CAS# | Product Structures | May be Prepared by the Method of (substituting the indicated starting diamine) |
|---|---|---|---|
| 46 | 1,7-diazaspiro[3.5]nonane CAS# 25408-26-8 | 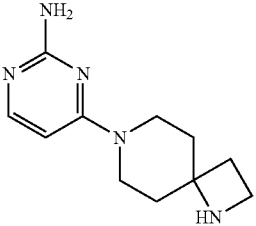 [SMILES: Nc1nccc(N2CCC3(CCN3)CC2)n1] | Example 3, 5 equivalents of diamine |
| 47 | tert-butyl 3-(aminomethyl)azetidine-1-carboxylate CAS# 325775-44-8 | 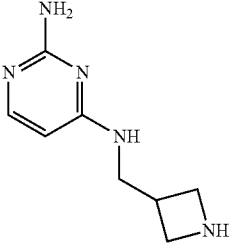 [SMILES: Nc1nccc(NCC2CNC2)n1] | Example 7A followed by Example 7B |
| 48 | tert-butyl azetidin-3-ylmethylcarbamate CAS# 91188-15-7 | 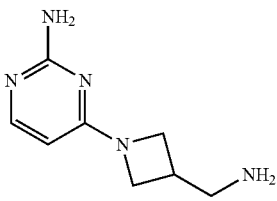 [SMILES: NCC1CN(c2ccnc(N)n2)C1] | Example 7A followed by Example 7B |
| 49 | tert-butyl azetidin-3-ylmethylcarbamate CAS# 99724-21-7 | 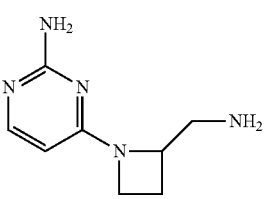 [SMILES: NCC1CCN1c1ccnc(N)n1] | Example 7A followed by Example 7B |
| 50 | (R)-tert-butyl 2-(aminomethyl)azetidine-1-carboxylate CAS# 887626-82-6 | 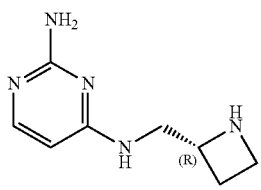 | Example 7A followed by Example 7B |
| 51 | (S)-tert-butyl 2-(aminomethyl)azetidine-1-carboxylate CAS# 1007873-90-6 | 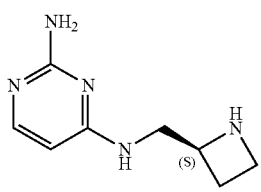 | Example 7A followed by Example 7B |

Determination of Biological Activity

To determine the effectiveness of representative compounds of this invention as histamine-3 receptor ligands ($H_3$ receptor ligands), the following tests were conducted according to previously described methods (see *European Journal of Pharmacology* 1990, 188, 219-227; *Journal of Pharmacology and Experimental Therapeutics* 1995, 275, 598-604; *Journal of Pharmacology and Experimental Therapeutics* 1996, 276, 1009-1015; and *Biochemical Pharmacology* 1973, 22, 3099-3108).

Radioligand Competition Binding Assay

The rat $H_3$ receptor was cloned and expressed in cells, and competition binding assays carried out, according to methods previously described (see Esbenshade, et al. *Journal of Pharmacology and Experimental Therapeutics* 2005, 313, 165-175; Esbenshade et al., *Biochemical Pharmacology* 2004, 68, 933-945; and Krueger, et al. *Journal of Pharmacology and Experimental Therapeutics* 2005, 314, 271-281). Membranes were prepared from C6 or HEK293 cells, expressing the rat histamine $H_3$ receptor, by homogenization on ice in TE buffer (50 mM Tris-HCl buffer, pH 7.4, containing 5 mM EDTA), 1 mM benzamidine, 2 μg/ml aprotinin, 1 μg/ml leupeptin, and 1 μg/ml pepstatin. The homogenate was centrifuged at 40,000 g for 20 minutes at 4° C. This step was repeated, and the resulting pellet was resuspended in TE buffer. Aliquots were frozen at −70° C. until needed. On the day of assay, membranes were thawed and diluted with TE buffer.

Membrane preparations were incubated with [$^3$H]-N-α-methylhistamine (0.5-1.0 nM) in the presence or absence of increasing concentrations of ligands for $H_3$ receptor competition binding. The binding incubations were conducted in a final volume of 0.5 ml TE buffer at 25° C. and were terminated after 30 minutes. Thioperamide (30 μM) was used to define non-specific binding. All binding reactions were terminated by filtration under vacuum onto polyethylenimine (0.3%) presoaked Unifilters (Perkin Elmer Life Sciences) or Whatman GF/B filters followed by three brief washes with 2 ml of ice-cold TE buffer. Bound radiolabel was determined by liquid scintillation counting. For all of the radioligand competition binding assays, $IC_{50}$ values and Hill slopes were determined by Hill transformation of the data and $pK_i$ values were determined by the Cheng-Prusoff equation.

Generally, representative compounds of the invention demonstrated binding affinities in the above assay from about 0.1 nM to about 3,100 nM. Preferred compounds of the invention bound to histamine-3 receptors with binding affinities from about 0.1 nM to about 20 nM. More preferred compounds of the invention bound to histamine-3 receptors with binding affinities from about 0.1 nM to about 2.0 nM.

TABLE 3

In vitro histamine $H_3$ receptor binding affinity

| Example # | Human $K_i$ (nM) | Rat $K_i$ (nM) |
|---|---|---|
| 1 | 63.1 | 5.50 |
| 2 | 53.7 | 20.0 |
| 3 | 257 | >309 |
| 4 | >331 | 162 |
| 5 | >339 | >316 |
| 6 | 61.7 | 13.2 |
| 7 | 28.2 | 81.3 |
| 8 | 316 | 195 |
| 9 | 182 | >309 |
| 10 | 178 | 162 |
| 11 | >339 | >316 |
| 12 | 72.4 | 24.5 |
| 13 | 13.8 | 7.41 |
| 14 | >380 | >355 |
| 15 | >355 | >331 |
| 16 | >363 | 141 |
| 17 | >363 | >339 |
| 18 | >363 | 162 |
| 19 | 158 | 170 |
| 20 | 302 | 58.9 |
| 21 | 162 | 55.0 |
| 22 | 33.1 | 97.7 |
| 23 | 67.6 | 12.3 |
| 24 | 324 | 105 |
| 25 | 24.0 | 5.75 |

FLIPR Functional Assay

There are many methods available to show the effectiveness of compounds as histamine $H_3$ receptor ligands. Histamine $H_3$ receptors from mammalian species have been cloned. Methods to clone, express, and assess the potency and functional activity of such cloned genes are well known to those skilled in the art of molecular biology. Examples of methods of cloning and expressing histamine $H_3$ receptors, and of assessing the potency and functional activity are described in Lovenberg, et al., *Molecular Pharmacology* 1999, 55, 1101-1107. In the present case, to determine the potency and effectiveness of representative compounds of this invention as histamine-$H_3$ receptor ligands ($H_3$ receptor ligands), the following tests were conducted according to previously described methods (see Esbenshade, et al., *Journal of Pharmacology and Experimental Therapeutics* 2003, 305, 887-896, Esbenshade, et al., *Biochemical Pharmacology* 2004, 68, 933-945, and in Krueger, et al., *Journal of Pharmacology and Experimental Therapeutics* 2005, 314, 271-281): histamine $H_3$ receptors were cloned and stably expressed in HEK-293 (human embryonic kidney) cells coexpressing a Gαqi5. Before testing, cells were loaded with a $Ca^{+2}$ sensitive fluorescent dye, in this case Fluo-4. For partial agonist or full agonist ligands, addition of compound to the cells led to an increase in intracellular $Ca^{+2}$ which was detected by FLIPR (Fluorescence Imaging Plate Reader; Molecular Devices, Sunnyvale, Calif.) technology. The fluorescence intensities measured before addition of the test compound were subtracted from the fluorescence intensities at later time points. Peak response values determined at each concentration of ligand were expressed as a percentage of the response obtained with a maximal concentration (1 μM) of the full agonist R-α-methyl-histamine (RAMH). Concentration versus response data were analyzed to obtain compound potency as $EC_{50}$ values for full and partial agonists.

TABLE 4

In vitro histamine $H_3$ receptor agonist potency of compounds in FLIPR

| | Human | | Rat | |
|---|---|---|---|---|
| Example # | $EC_{50}$ (nM) | Maximum (%)* | $EC_{50}$ (nM) | Maximum (%)* |
| 1 | 124 | 60.2 | 5.47 | 100.0 |
| 2 | 85.1 | 77.7 | | |
| 6 | 13.4 | 93.0 | | |
| 14 | 316 | 67.6 | | |
| 15 | 43.6 | 39.0 | | |
| 16 | 17,660 | 34.2 | 448 | 74.0 |

TABLE 4-continued

In vitro histamine $H_3$ receptor agonist potency of compounds in FLIPR

| | Human | | Rat | |
|---|---|---|---|---|
| Example # | $EC_{50}$ (nM) | Maximum (%)* | $EC_{50}$ (nM) | Maximum (%)* |
| 17 | | | 4,786 | 75.8 |
| 18 | | | 74.0 | 78.6 |
| 19 | 2,113 | 50.2 | | |
| 20 | 254 | 41.0 | 51.7 | 83.0 |

*For reference, the $H_3R$ agonist, histamine, has the following human Maximum: 116% and rat Maximum: 98.4%.

Generally, representative compounds of the invention demonstrated potencies in the above FLIPR assay from about 4 nM to about 18,000 nM. Preferred compounds of the invention have potencies at histamine-$H_3$ receptors from about 4 nM to about 700 nM. More preferred compounds of the invention have potencies at histamine $H_3$ receptors from about 4 nM to about 200 nM.

GTPγS Functional Assay

Membranes from HEK cells expressing the human $H_3R$, or from C6 cells expressing the rat $H_3R$, were prepared by homogenization in cold buffer containing 50 mM Tris-HCl (pH 7.4), 5 mM EDTA, 10 mM $MgCl_2$, 1 mM benzamidine, 2 µg/ml aprotinin, 1 µg/ml leupeptin, and 1 µg/ml pepstatin. The homogenate was centrifuged at 40,000 g for 20 min at 4° C., and the resulting pellet was resuspended in 50 mM Tris-HCl (pH 7.4), 5 mM EDTA, and 10 mM $MgCl_2$ and homogenized. Glycerol and bovine serum albumin were added to a final concentration of 10% glycerol and 1% bovine serum albumin. Membranes were diluted in GTPγS assay buffer (25 mM HEPES, 2.5 mM $MgCl_2$, and 75 mM NaCl, pH 7.4) and 10 µg of membrane protein was incubated in a 96-well deep-well block in the presence of 5.0 µM unlabeled GDP, approximately 0.5 nM of [$^{35}$S]GTPγS, and increasing concentrations of test compounds. Samples were incubated at 37° C. for 5 min and the assays were terminated by the addition of cold buffer (50 mM Tris-HCl, 75 mM NaCl, and 2.5 mM $MgCl_2$, pH 7.6) and subsequent harvesting onto a Packard Unifilter 96-well GF/B plate followed by extensive washing. Microscint 20 (PerkinElmer Life Sciences) was added to the samples, and bound [$^{35}$S]GTPγS was determined using the Topcount (Perkin Elmer Life Sciences). The percentage of [$^{35}$S]GTPγS bound in each sample was calculated as a percentage of that bound to control samples incubated in the absence of the $H_3R$ agonists (basal). Data were analyzed from experiments performed in triplicate using GraphPad Prism to obtain p$EC_{50}$ values, Hill slopes, and maximal % response.

TABLE 5

In vitro histamine $H_3$ receptor agonist potency of compounds in GTPγS

| | Human | | Rat | |
|---|---|---|---|---|
| Example # | $EC_{50}$ (nM) | Maximum (%)* | $EC_{50}$ (nM) | Maximum (%)* |
| 1 | 513 | 147 | 174 | 181 |
| 2 | 525 | 160 | 339 | 183 |
| 4 | 2,291 | 150 | 1,413 | 161 |
| 5 | 4,266 | 132 | 3,802 | 165 |
| 6 | 537 | 162 | 309 | 168 |
| 9 | | | 1,950 | 110 |
| 10 | | | 955 | 139 |
| 11 | 5,754 | 111 | | |
| 12 | 871 | 139 | 324 | 136 |
| 13 | 129 | 127 | 53.7 | 135 |
| 15 | 4,786 | 117 | 7,413 | 138 |
| 17 | | | 2,344 | 130 |
| 18 | 2,512 | 179 | 1,622 | 162 |
| 19 | | | 447 | 116 |
| 20 | 1,047 | 122 | 724 | 123 |
| 21 | 115 | 120 | 214 | 135 |
| 22 | 457 | 216 | 676 | 156 |
| 23 | 513 | 147 | 110 | 126 |
| 25 | 132 | 150 | 30.2 | 141 |

*For reference, the selective $H_3R$ agonist, R-α-methyl-histamine (RAMH), has the following human Maximum: 240% and rat Maximum: 224%.

In Vivo Functional Assessment of Histamine $H_3$ Receptor Agonists in the Mouse Dipsogenia Model Intraperitoneal administration of an $H_3$ receptor agonist such as R-alpha-methyl-histamine elicits drinking in the hydrated CD-1 mouse (Fox, G. B.; et al. *Pharmacology Biochemistry and Behavior* 2002, 72, 741-750). This dipsogenic response is an indication of agonist activity in vivo and can be monitored by measuring the water intake of drug-treated animals in a 30 minute period. Administration of Example 1 dose dependently (80, 160, and 240 µmol/kg, ip) induced water intake in this model. The dipsogenic response to Example 1 (240 µmol/kg, ip) was blocked by the $H_3$ receptor antagonist, ciproxifan (3 µmol/kg, ip).

$H_3R$ Agonist Sleep Study in Rats: Assessment of Cortical Low Frequency EEG Amplitude in the 1-4 Hz Band (Delta)

All experiments were conducted with male adult CD-1 rats of the Sprague-Dawley strain (Charles River Laboratories, Portage, Mich.) with body weights in the range of 400-600 g. When the rats were not in the laboratory being tested, they were housed 1 per cage in a climate controlled room with 12 hour lights on, 12 hour lights off cycle and food provided ad-lib.

For anesthesia during surgical implantation of EEG recording electrodes, rats were administered Nembutal (Abbott Laboratories) 50 mg/ml ip. After achieving a deep, stable plane of anesthesia, scalp hair was removed using electric clippers and the rat was placed into the ear and incisor bars of a stereotaxic instrument to immobilize the head. The scalp was disinfected with povidone iodine, and an incision was placed longitudinally along the midline of the scalp and the tissue retracted from the skull with a blunt probe. EEG recording electrodes were bilaterally implanted over the parietal (−2.0 mm anterior-posterior, 4.0 mm lateral from bregma) and frontal (+2.0 mm anterior-posterior, 3.0 mm lateral from bregma) cortices. A reference electrode was placed 11.0 mm posterior to bregma along the centerline (0.0 mm lateral). Cortical surface electrodes consist of stainless steel screws (size #90-00) was soldered to a fine silver wire and a miniature electrical socket. To implant the electrodes, small holes were drilled (#60 bit) into the skull, taking care not to damage the dura membrane covering the cerebrum with the drill bit. The surface electrodes were screwed into the holes to a depth that comes in contact with, but did not penetrate the dura. Once in place, the electrodes along with the miniature connector were permanently affixed to the skull with acrylic dental cement. The rats were given a 10-14 day recovery period from the surgery before experiments were conducted.

The EEG was recorded from rats inside sound-attenuating chambers (Med Associates Inc, St. Albans, Vt.). Before any pharmacological experiments began, implanted rats were habituated to the EEG recording chambers for 2-5 hours on 5 consecutive days. When placed into the recording chambers, a flexible cable was attached to the miniature connector implanted on the rats. This cable allowed the rat unrestricted movement within the chamber during the EEG recording session. EEG amplifiers (AM Systems, Inc., Carlsborg, Wash.) and a computer-based data acquisition system (Datawave Inc., Berthoud, Colo.) were used to acquire (256 Hz sampling rate) and analyze data. All experiments and habituation sessions were conducted during the light phase of the circadian cycle.

Each rat received a vehicle control treatment (placebo), and all doses of the test compounds. All doses are expressed in mg/kg of free base of the compounds. For use, test compounds were dissolved in sterile water –1% citric acid solution (pH ~5.3). The sterile water –1% citric acid solution served as the vehicle control (placebo) treatment for the compounds. All treatments were administered by the intraperitoneal (i.p.) route of administration. The treatments were administered in a random order on different days with one treatment per day, and at least 2 days between treatments. This within subjects design allowed each rat to serve as its own control. EEG recordings began within 10 minutes after injection and recording sessions lasted for 300 minutes. The time of day for injections and subsequent recordings were between 10:00 AM and 2:00 PM.

Assessment of cortical low frequency EEG amplitude in the 1-4 Hz band (delta) was used as an electrophysiological measure of $H_3R$ agonist activity in rats. The 1-4 Hz EEG amplitude in microvolts ($\mu V$) was determined for each 10 second epoch of EEG during the 300 minute recording sessions using Fast Fourier Transform (FFT) analysis. Three hundred and sixty (360) consecutive 10-second amplitude determinations were then averaged to derive an average 1-4 Hz EEG amplitude for each 60 minute period following injection of drug. Epochs that contained movement artifact in the EEG were excluded from this averaging (<5% of all epochs). A repeated measure, one-way ANOVA was utilized for statistical evaluation of average FFT data with treatment as the repeated measure. A Newman-Keuls post-hoc test was used for comparisons between treatments. The average 1-4 Hz amplitude data for the two hours of EEG recording was graphically expressed as in FIG. 1 for Example 1.

$H_3R$ Agonist Pain Study in Mice: Acetic Acid-Induced Writhing

Intraperitoneal injection of 0.9% acetic acid induces a writhing response that is quantified by counting the number of these induced characteristic lengthwise abdominal constrictions with torso elongations in a fixed time period (Langford, D. J.; et al. *Science* 2006, 312, 1967-1970). Reduction of the number of writhes by a compound administered 30 minutes prior to acetic acid exposure is a measure of analgesic activity. Example 1 significantly reduced the number of writhes at a subcutaneous dose of 300 mg/kg.

Compounds of the invention are histamine-3 receptor ligands that modulate function of the histamine-3 receptor by altering the activity of the receptor. These compounds may be partial agonists that partially activate the histamine-3 receptor or they may be full agonists that fully activate the receptor.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (IV) or a pharmaceutically acceptable salt thereof,

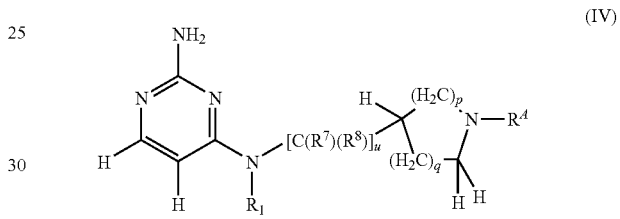

wherein $R^4$ is hydrogen, alkyl, arylalkyl, alkoxycarbonyl, or cycloalkyl, $R^1$ is hydrogen or methyl, $R^7$ and $R^8$ are each independently hydrogen or lower alkyl, u is 0, p is an integer from 0 to 2, and q is an integer from 0 to 2, provided that p and u are not both equal to 0.

2. The compound of claim 1, selected from the group consisting of:
   $N^4$-(1-benzylpiperidin-4-yl)pyrimidine-2,4-diamine;
   (R)-tert-butyl 3-(2-aminopyrimidin-4-ylamino)pyrrolidine-1-carboxylate;
   (R)—$N^4$-(pyrrolidin-3-yl)pyrimidine-2,4-diamine;
   $N^4$-(azetidin-3-yl)pyrimidine-2,4-diamine; and
   $N^4$-(piperidin-4-yl)pyrimidine-2,4-diamine;
or a pharmaceutically acceptable salt thereof.

3. A pharmaceutical composition comprising a therapeutically effective amount of a compound of claim 1, or a pharmaceutically acceptable salt thereof.

* * * * *